United States Patent
Valdivia et al.

(10) Patent No.: US 10,689,644 B2
(45) Date of Patent: Jun. 23, 2020

(54) SYSTEMS AND METHODS FOR GENETIC ANALYSIS OF INTRACTABLE MICROBES

(71) Applicant: Duke University, Durham, NC (US)

(72) Inventors: Raphael Valdivia, Carrboro, NC (US); Sena Bae, Durham, NC (US)

(73) Assignee: Duke University, Durham, NC (US)

(*) Notice: Subject to any disclaimer, the term of this patent is extended or adjusted under 35 U.S.C. 154(b) by 0 days.

(21) Appl. No.: 15/462,749

(22) Filed: Mar. 17, 2017

(65) Prior Publication Data

US 2017/0306321 A1    Oct. 26, 2017

Related U.S. Application Data

(60) Provisional application No. 62/309,669, filed on Mar. 17, 2016.

(51) Int. Cl.
```
C12N 15/10     (2006.01)
A61K 35/74     (2015.01)
G16B 20/00     (2019.01)
G16B 20/50     (2019.01)
```

(52) U.S. Cl.
CPC .......... *C12N 15/1079* (2013.01); *A61K 35/74* (2013.01); *C12N 15/1065* (2013.01); *G16B 20/00* (2019.02); *G16B 20/50* (2019.02)

(58) Field of Classification Search
CPC .................................................. C12N 15/10; C12N 15/1079; C12N 15/1065; A61K 35/74; G06F 19/18
USPC ........ 435/4, 7.31, 7.32, 29, 32, 34, 822, 911
See application file for complete search history.

(56) References Cited

PUBLICATIONS

Harper et al., (PLOS One. Feb. 2014. vol. 9. Issue 2. e88072, pp. 1-10) in view of Dasgupta et al., ( J. Bacteriol. Jan. 2000; 182(2):357-364).*
Dasgupta et al., ( J. Bacteriol. Jan. 2000; 182(2):357-364).*
Koshkiniemi et al., (POLS One. Jul. 2013. vol. 8. Issue 7, e70147, pp. 1-10).*
Fong et al., (Genome Res. 2005. 15: 1365-1372). (Year: 2005).*
Matsuyama et al., (J. of Bacteriol. Feb. 1995. vol. 177, No. 4, p. 987-991) (Year: 1995).*
Cousin et al., (Applied and Environ. Micro. Feb. 2015. Published online Dec. 2014. vol. 81. Nu: 4. pp. 1297-1308). (Year: 2014).*
Neville et al., (PLOS ONE.vol. 8. Issue 7. Published Jul. 23, 2013. e68919; pp. 1-15). (Year: 2013).*
Amati et al., "DegU-P represses expression of the motility fla-che operon in Bacillus subtilis," J Bacteriol, 2004, 186(18):6003-6014.

(Continued)

*Primary Examiner* — Jana A Hines
(74) *Attorney, Agent, or Firm* — Michael Best & Friedrich LLP

(57) ABSTRACT

Embodiments of the present disclosure relate generally to the genetic analysis of intractable microbes. More particularly, the present disclosure provides materials and methods that incorporate chemical mutagenesis, phenotypic selection, suppression analysis, and genomic sequencing-based mutational mapping, to identify novel genetic regulators in previously intractable organisms, such as microbes that constitute the human microbiome. Given the paucity of experimental tools to manipulate bacterial genomes, there is a need for improved methods for determining how microbial communities assemble and influence human and environmental health.

11 Claims, 10 Drawing Sheets

Specification includes a Sequence Listing.

(56) References Cited

PUBLICATIONS

Boehm et al., "Second messenger-mediated adjustment of bacterial swimming velocity," Cell, 2010, 141(1):107-116.

Cairns et al., "FlgN is required for flagellum-based motility by Bacillus subtilis," J Bacteriol, 2014, 196(12):2216-2226.

Carpenter et al., "Bacillus subtilis FlhA: a flagellar protein related to a new family of signal-transducing receptors," Mol Microbiol, 1993, 7(5):735-743.

Chen et al., "Evidence for cyclic Di-GMP-mediated signaling in Bacillus subtilis," J Bacteriol, 2012, 194(18):5080-5090.

Chen et al., "Role of the sigmaD-dependent autolysins in Bacillus subtilis population heterogeneity," J Bacteriol, 2009, 191(18):5775-5784.

Cullender et al., "Innate and adaptive immunity interact to quench microbiome flagellar motility in the gut," Cell Host Microbe, 2013, 14(5):571-581.

Edgar, "Search and clustering orders of magnitude faster than BLAST," Bioinformatics, 2010, 26:2460-2461.

Erhardt, "Strategies to Block Bacterial Pathogenesis by Interference with Motility and Chemotaxis," Curr Top Microbiol Immunol, 2016, pp. 186-205.

Gao et al., "Functional characterization of core components of the Bacillus subtilis cyclic-di-GMP signaling pathway," J Bacteriol, 2013, 195(21):4782-4792.

Garti-Levi et al., "The FtsEX ABC transporter directs cellular differentiation in Bacillus subtilis," Mol Microbiol, 2008, 69(4):1018-1028.

Girgis et al., "A comprehensive genetic characterization of bacterial motility," PLoS Genet, 2007, 3:1644-1660.

Goodman et al., "Identifying genetic determinants needed to establish a human gut symbiont in its habitat," Cell Host Microbe, 2009, 6(3):279-289.

Guttenplan et al., "Regulation of flagellar motility during biofilm formation," FEMS Microbiol Rev, 2013, 37(6):849-871.

Henry et al., "Ligand-binding PAS domains in a genomic, cellular, and structural context," Annu Rev Microbiol, 2011, 65:261-286.

Kempf et al., "Transposon insertions in the Flavobacterium johnsoniae ftsX gene disrupt gliding motility and cell division," J Bacteriol, 2000, 182(6):1671-1679.

Langmead et al., "Fast gapped-read alignment with Bowtie 2," Nat Methods, 2012, 9:357-359.

Levefaudes et al., "Diaminopimelic Acid Amidation in Corynebacteriales: New Insights Into the Role of LtsA in Peptidoglycan Modification," J Biol Chem, 2015, 290(21):13079-13094.

Libby et al., "The Eukaryotic-Like Ser/Thr Kinase PrkC Regulates the Essential WalRK Two-Component System in Bacillus subtilis," PLoS Genet, 2015, 11(6):e1005275.

Malapaka et al., "High-throughput screening for antimicrobial compounds using a 96-well format bacterial motility absorbance assay," J Biomol Screen, 2007, 12:849-854.

McFall-Ngai et al., "Animals in a bacterial world, a new imperative for the life sciences," Proc Natl Acad Sci U S A, 2013, 110(9):3229-3236.

Meisner et al., "FtsEX is required for CwlO peptidoglycan hydrolase activity during cell wall elongation in Bacillus subtilis," Mol Microbiol, 2013, 89(6):1069-1083.

Mukherjee et al., "The structure and regulation of flagella in Bacillus subtilis," Annu Rev Genet, 2014, 48:319-340.

Neumann et al., "Chemotactic signaling via carbohydrate phosphotransferase systems in Escherichia coli," Proc Natl Acad Sci U S A, 2012, 109(30):12159-12164.

Nguyen et al., "Virulence determinants in the obligate intracellular pathogen Chlamydia trachomatis revealed by forward genetic approaches," Proc Natl Acad Sci U S A, 2012, 109(4):1263-1268.

Nieuwdorp et al., "Role of the microbiome in energy regulation and metabolism," Gastroenterology, 2014, 146(6):1525-1533.

Pandini et al., "Coevolved Mutations Reveal Distinct Architectures for Two Core Proteins in the Bacterial Flagellar Motor," PLoS One, 2015, 10(11):e0142407.

Park et al., "Structure of FliM provides insight into assembly of the switch complex in the bacterial flagella motor," Proc Natl Acad Sci U S A, 2006, 103(32):11886-11891.

Paul et al., "The c-di-GMP binding protein YcgR controls flagellar motor direction and speed to affect chemotaxis by a "backstop brake" mechanism," Mol Cell, 2010, 38(1):128-139.

Pham et al., "Methods for generating and colonizing gnotobiotic zebrafish," Nat Protoc, 2008, 3:1862-1875.

Rahn-Lee et al., "A genetic strategy for probing the functional diversity of magnetosome formation," PLoS Genet, 2015, 11(1):e1004811.

Rawls et al., "In vivo imaging and genetic analysis link bacterial motility and symbiosis in the zebrafish gut," Proc Natl Acad Sci U S A, 2007, 104(18):7622-7627.

Rawls et al., "Reciprocal gut microbiota transplants from zebrafish and mice to germ-free recipients reveal host habitat selection," Cell, 2006, 127(2):423-433.

Robins et al., "Coupling mutagenesis and parallel deep sequencing to probe essential residues in a genome or gene," Proc Natl Acad Sci U S A, 2013, 110(9):E848-857.

Ryan et al., "The DSF Family of Cell-Cell Signals: An Expanding Class of Bacterial Virulence Regulators," PLoS Pathog, 2015, 11(7):e1004986.

Samant et al., "The Bacillus anthracis protein MprF is required for synthesis of lysylphosphatidylglycerols and for resistance to cationic antimicrobial peptides," J Bacteriol, 2009, 191(4):1311-1319.

Schirmer et al., "Structural and mechanistic determinants of c-di-GMP signaling," Nat Rev Microbiol, 2009, 7(10):724-735.

Schwab et al., "Longitudinal study of murine microbiota activity and interactions with the host during acute inflammation and recovery," ISME J, 2014, 8(5):1101-1114.

Seemann, "Prokka: rapid prokaryotic genome annotation," Bioinformatics, 2014, 30:2068-2069.

Semova et al., "Microbiota regulate intestinal absorption and metabolism of fatty acids in the zebrafish," Cell Host Microbe, 2012, 12(3):277-288.

Szurmant et al., "Bacillus subtilis CheC and FliY are members of a novel class of CheY-P-hydrolyzing proteins in the chemotactic signal transduction cascade," J Biol Chem, 2004, 279(21):21787-21792.

Tuckerman et al., "An oxygen-sensing diguanylate cyclase and phosphodiesterase couple for c-di-GMP control," Biochemistry, 2009, 48(41):9764-9774.

Vishnivetskaya et al., "Draft genome sequences of 10 strains of the genus Exiguobacterium," Genome Announc, 2014, 2(5).

Wei et al., "SNVer: a statistical tool for variant calling in analysis of pooled or individual next-generation sequencing data," Nucleic Acids Res, 2011, 39:e132.

Wride et al., "Confirmation of the cellular targets of benomyl and rapamycin using next-generation sequencing of resistant mutants in S. cerevisiae," Mol Biosyst, 2014, 10(12):3179-3187.

Wu et al., "Genetic determinants of in vivo fitness and diet responsiveness in multiple human gut Bacteroides," Science, 2015, 350(6256):aac5992.

Zuberi et al., "Gene-protein relationships in the flagellar hook-basal body complex of Bacillus subtilis: sequences of the flgB, flgC, flgG, fliE and fliF genes," Gene, 1991, 101(1):23-31.

Zuberi et al., "Nucleotide sequence and characterization of a Bacillus subtilis gene encoding a flagellar switch protein," J Bacteriol, 1991, 173(2):710-719.

* cited by examiner

FIG. 6A
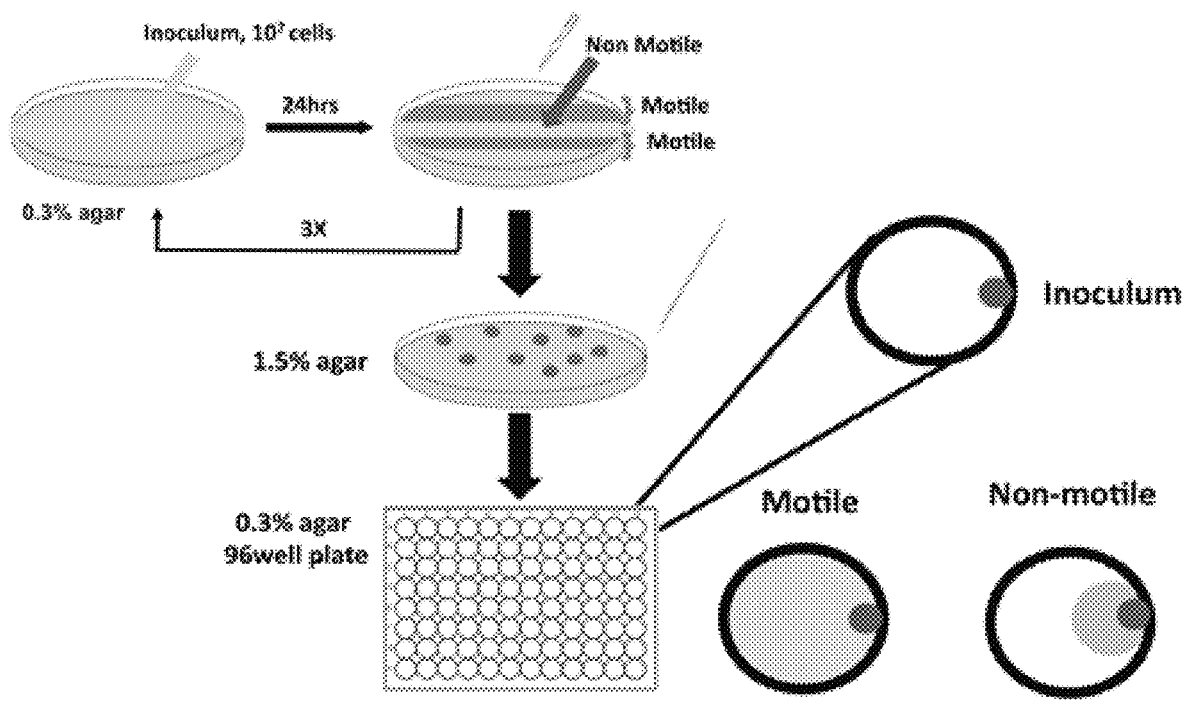
FIG. 6B
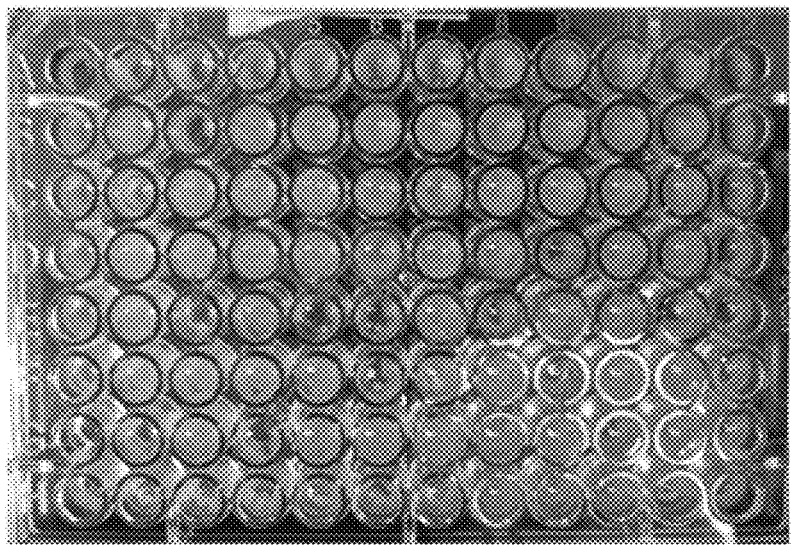
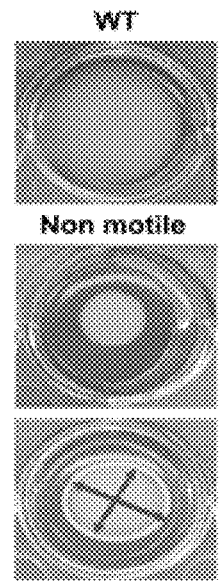
FIG. 6C

SYSTEMS AND METHODS FOR GENETIC ANALYSIS OF INTRACTABLE MICROBES

RELATED APPLICATIONS

This application claims priority to and the benefit of U.S. Provisional Patent Application Ser. No. 62/309,669, entitled "Systems and Methods for Mining Microbial Genomes for Biologically Active Compounds," filed Mar. 17, 2016. U.S. Provisional Patent Application Ser. No. 62/309,669 is incorporated herein by reference in its entirety for all purposes.

FIELD

Embodiments of the present disclosure relate generally to the genetic analysis of intractable microbes. More particularly, the present disclosure provides materials and methods that incorporate chemical mutagenesis, phenotypic selection, suppression analysis, and genomic sequencing-based mutational mapping, to identify novel genetic regulators in previously intractable organisms, such as microbes that constitute the human microbiome.

BACKGROUND

The advent of DNA-sequence-based approaches to analyze microbial environments has led to a deepened appreciation for the diversity, ubiquity, and functions of microbial life. For instance, the gastrointestinal tract of humans and other vertebrates is colonized by complex microbial communities that promote gut development, nutrient metabolism, and immune homeostasis. Of particular importance to human health, gut microbes have emerged as major risk determinants for obesity and metabolic disorders, in part because of their role in modulating accessibility and absorption of energy-rich dietary nutrients in vertebrates. For example, colonization of germ-free zebrafish with *Exiguobacterium* sp. ZWU0009, a Firmicutes bacterium originally isolated from the zebrafish intestine, enhanced the ability of intestinal enterocytes to absorb dietary fat. Unfortunately, the molecular bases for how bacteria like *Exiguobacterium* sp. ZWU0009 colonize the intestine and influence host physiology are poorly understood.

Indeed, most microbes are not amenable to genetic manipulation because methods for robust DNA transformation, insertional mutagenesis, and trans-expression of genes are largely lacking. For a select group of microbial species, including members of the Bacteroides genus, some strains are amenable to transposon mutagenesis and have been invaluable in helping decipher the requirement of individual genes in gut colonization and nutrient homeostasis. However, genetic tools do not exist for the vast majority of intestinal microbes. As a result, the function of individual genes and their contribution to host-microbe and microbe-microbe interactions within the gut often relies on information inferred from homology to genes characterized in phylogenetically unrelated, but genetically tractable, bacterial systems. This reliance on previously characterized genes is a significant challenge that inhibits the functional annotation of novel genes emerging from metagenomic studies, as well as impairs the ability to identify new targets for the development of therapeutic compounds and treatments.

Given the paucity of experimental tools to manipulate bacterial genomes, there is a need for improved methods for determining how microbial communities assemble and influence human and environmental health. Embodiments of the present disclosure address these and other needs.

SUMMARY

Embodiments of the present disclosure relate generally to the genetic analysis of intractable microbes. More particularly, the present disclosure provides materials and methods that incorporate chemical mutagenesis, phenotypic selection, suppression analysis, and genomic sequencing-based mutational mapping, to identify novel genetic regulators in previously intractable organisms, such as microbes that constitute the human microbiome.

Embodiments of the present disclosure include methods of identifying a genetic regulator of a trait in a microbe affecting host colonization, including exposing a microbe to a mutagen to produce a plurality of mutagenic variants, performing phenotype-based assessment of the mutagenic variants based on at least one trait, sequencing at least a portion of the plurality of mutagenic variants' genomes, and determining differences in the genomic sequences of the plurality of mutagenic variants as compared to a reference genome, wherein the differences in the genomic sequences between the plurality of mutagenic variants and the reference genome are indicative of a genetic regulator of the trait affecting host colonization.

The methods according to this paragraph, further comprising performing bioinformatics analysis to identify known genetic regulators of the trait, and determining differences between the sequences of the known genetic regulators and the genomic sequences of the plurality of mutagenic variants.

The methods according to either the this paragraph or the above, further comprising performing suppression-bases analysis of the plurality of mutagenic variants comprising: passaging one or more of the plurality of mutagenic variants at least three times; and performing phenotype-based assessment of the one or more of the plurality of mutagenic variants to identify variants exhibiting the desired phenotype based on the trait.

The methods according to any of the above paragraphs, wherein the mutagen is a selected from the group consisting of ethyl methyl sulfonate (EMS), methyl methane sulphonate (MMS), nitrous acid, N-ethyl-N'-nitro-N-nitrosoguanidine (ENNG), 1,2-dibromoethane (DBE), 1-chloro-2,4-dinitrobenzene (CDNB), styrene-7,8-oxide (STOX), N-ethyl-N-nitrosourea (ENU), radiation and ultraviolet light.

The methods according to any of the above paragraphs, wherein the microbe is a bacteria selected from a group consisting of: *Acidovorax, Acinetobacter, Agrobacterium, Akkermansia, Alistipes, Allobaculum, Aquabacterium, Azonexus, Bacillaceae* 1, *Bryantella, Carnobacteriaceae* 1, *Chryseobacterium, Chryseomonas, Cloacibacterium, Comamonas, Dechloromonas, Delftia, Enterobacter, Erwinia, Exiguobacterium, Flavimonas, Fusobacterium,* Gp1, Gp2, *Helicobacter, Lactobacillus, Lactococcus, Leuconostoc, Methylobacterium, Micrococcineae, Novosphingobium, Pantoea, Pseudomonas, Pseudoxanthomonas, Roseburia, Rubrobacterineae, Serratia, Shinella, Sphingobium, Staphylococcus, Stenotrophomonas, Succinivibrio, Sutterella, Syntrophococcus, Turicibacter, Variovorax,* and *Weissella.*

The methods according to any of the above paragraphs, wherein the bacteria is from the genus *Exiguobacterium.*

The methods according to any of the above paragraphs, wherein the trait comprises at least one of motility, amino acid biosynthesis, carbohydrate metabolism, nutrient uptake, redox tolerance, secretion, adherence, invasion, respiration, growth, and reproduction.

The methods according to any of the above paragraphs, wherein sequencing at least a portion of the plurality of mutagenic variants' genomes comprises determining mutagen-induced single nucleotide variants (SNVs).

The methods according to any of the above paragraphs, wherein performing a phenotype-based assessment of the mutagenic variants comprises identifying the mutagenic variants that are non-motile.

The methods according to any of the above paragraphs, wherein the trait comprises motility, and wherein the genetic regulator is a gene known to be involved in flagellar function.

The methods according to any of the above paragraphs, wherein the genetic regulator is selected from the group consisting of: fliE, fliF, fliK, figG1, flhA, fliM, figN, and hag1.

The methods according to any of the above paragraphs, wherein the trait comprises motility, and wherein the genetic regulator is a gene not known to be involved in motility.

The methods according to any of the above paragraphs, wherein the genetic regulator is selected from the group consisting of: ftsX, ea2619, ea2862, and ea2157.

The methods according to any of the above paragraphs, wherein the host is a human.

Embodiments of the present disclosure also include methods of improving gut health in a subject, including exposing a microbe known to be a part of the gut microbiota of a subject to a mutagen to produce a plurality of mutagenic variants, performing phenotype-based assessment of the mutagenic variants based on at least one trait, sequencing at least a portion of the plurality of mutagenic variants' genomes, and determining differences in the genomic sequences of the plurality of mutagenic variants as compared to a reference genome, wherein the differences in the genomic sequences between the plurality of mutagenic variants and the reference genome are indicative of a genetic regulator of the trait, and treating the subject with a therapeutic agent that modulates the function of the genetic regulator of the trait, thereby improving gut health in the subject.

The methods according to this paragraph, further comprising performing bioinformatics analysis to identify known genetic regulators of the trait, and determining differences between the sequences of the known genetic regulators and the genomic sequences of the plurality of mutagenic variants.

The methods according to either the above or this paragraph, further comprising performing suppression-bases analysis of the plurality of mutagenic variants comprising: passaging one or more of the plurality of mutagenic variants at least three times; and performing phenotype-based assessment of the one or more of the plurality of mutagenic variants to identify variants exhibiting the desired phenotype based on the trait.

The methods according to any of the above paragraphs, wherein the microbe is a bacteria selected from a group consisting of: *Acidovorax, Acinetobacter, Agrobacterium, Akkermansia, Alistipes, Allobaculum, Aquabacterium, Azonexus, Bacillaceae* 1, *Bryantella, Carnobacteriaceae* 1, *Chryseobacterium, Chryseomonas, Cloacibacterium, Comamonas, Dechloromonas, Delftia, Enterobacter, Erwinia, Exiguobacterium, Flavimonas, Fusobacterium,* Gp1, Gp2, *Helicobacter, Lactobacillus, Lactococcus, Leuconostoc, Methylobacterium, Micrococcineae, Novosphingobium, Pantoea, Pseudomonas, Pseudoxanthomonas, Roseburia, Rubrobacterineae, Serratia, Shinella, Sphingobium, Staphylococcus, Stenotrophomonas, Succinivibrio, Sutterella, Syntrophococcus, Turicibacter, Variovorax,* and *Weissella*.

The methods according to any of the above paragraphs, wherein performing a phenotype-based assessment of the mutagenic variants comprises identifying the mutagenic variants that are non-motile.

The methods according to any of the above paragraphs, wherein the trait comprises motility, and wherein the genetic regulator is selected from the group consisting of: fliE, fliF, fliK, figG1, flhA, fZiM, figN, hag1, ftsX, ea2619, ea2862, and ea2157.

The methods according to any of the above paragraphs, wherein the subject is a human, and wherein modulating the function of the genetic regulator comprises improving motility and enhancing colonization of the microbe in the human gut.

BRIEF DESCRIPTION OF THE DRAWINGS

FIGS. 6A-6C include a schematic illustration of the isolation of non-motile *E. acetylicum* mutants (A); a representative image of a 96 well plate used to screen for motility defects (B); and a representative image of secondary confirmation tests for the loss of motility (C).

Figure 1A:
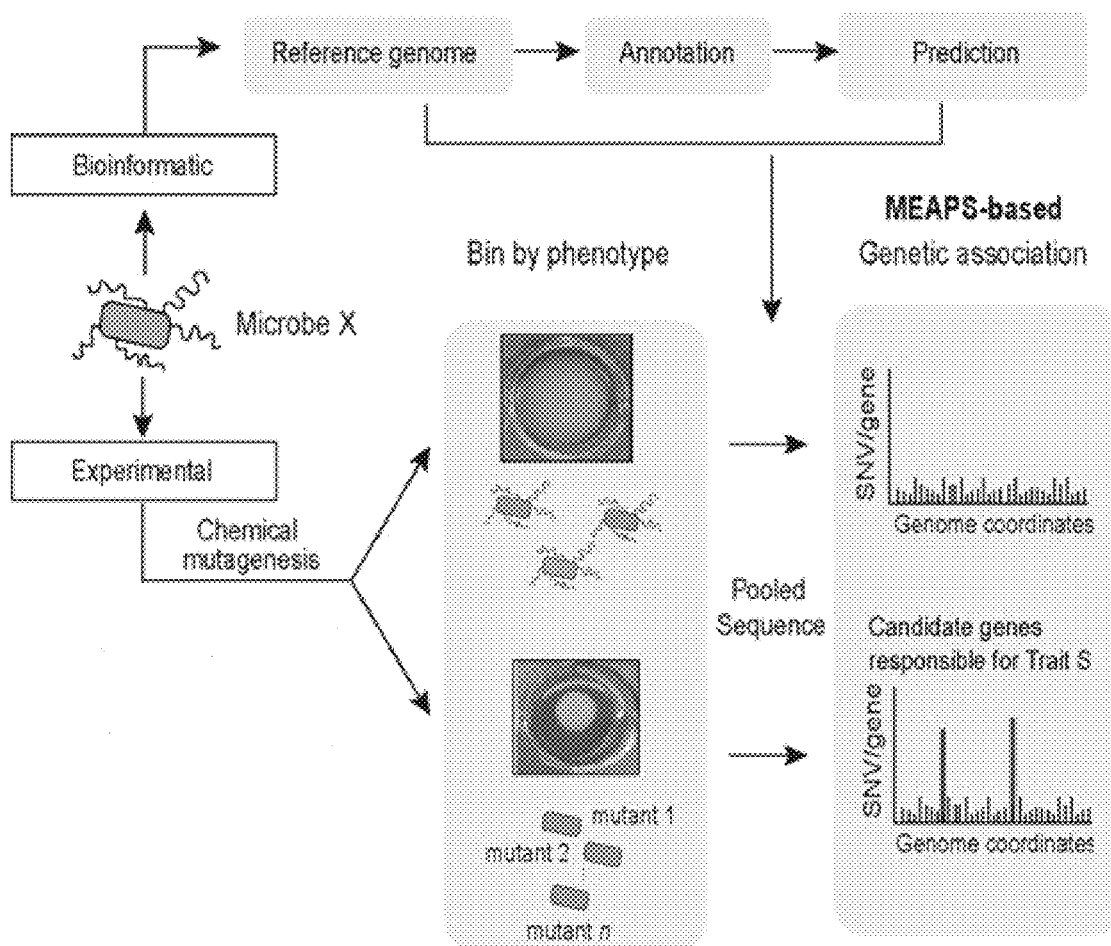
FIGS. 1A-1E include a representative schematic illustration of methods for identifying genes required for motility in *E. acetylicum* (A); representative transmission electron micrographs of *E. acetylicum* flagella (B; bar: 0.5 μM); MEAPS identification of *E. acetylicum* strains defective for motility (C); genetic mapping of ORFs in motility Region I (D); and a representative schematic of the Gram positive flagellar apparatus displaying all components conserved in *E. acetylicum* (E).

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "an" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

The use of the terms "a" and "an" and "the" and "at least one" and similar referents in the context of describing the invention (especially in the context of the following claims) are to be construed to cover both the singular and the plural, unless otherwise indicated herein or clearly contradicted by context. The use of the term "at least one" followed by a list of one or more items (for example, "at least one of A and B") is to be construed to mean one item selected from the listed items (A or B) or any combination of two or more of the listed items (A and B), unless otherwise indicated herein or clearly contradicted by context. The terms "comprising," "having," "including," and "containing" are to be construed as open-ended terms (i.e., meaning "including, but not limited to,") unless otherwise noted. Recitation of ranges of values herein are merely intended to serve as a shorthand method of referring individually to each separate value falling within the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the invention and does not pose a limitation on the scope of the invention unless otherwise claimed. No language in the specification should be construed as indicating any non-claimed element as essential to the practice of the invention.

As used herein, the terms "subject" and "patient" are used interchangeably irrespective of whether the subject has or is currently undergoing any form of treatment. As used herein, the terms "subject" and "subjects" refer to any vertebrate, including, but not limited to, a mammal (e.g., cow, pig, camel, llama, horse, goat, rabbit, sheep, hamsters, guinea pig, cat, dog, rat, and mouse, a non-human primate (for example, a monkey, such as a cynomolgous monkey, chimpanzee, etc.) and a human). In some aspects, the subject is a human.

The terms "treat," "treated," or "treating," as used herein, refer to a therapeutic method wherein the object is to slow down (lessen) an undesired physiological condition, disorder or disease, or to obtain beneficial or desired clinical results. In some aspects of the present disclosure, beneficial or desired clinical results include, but are not limited to, alleviation of symptoms; diminishment of the extent of the condition, disorder or disease; stabilization (i.e., not worsening) of the state of the condition, disorder or disease; delay in onset or slowing of the progression of the condition, disorder or disease; amelioration of the condition, disorder or disease state; and remission (whether partial or total), whether detectable or undetectable, or enhancement or improvement of the condition, disorder or disease. Treatment also includes prolonging survival as compared to expected survival if not receiving treatment.

Before any embodiments of the present disclosure are explained in detail, it is to be understood that the present disclosure is not limited in its application to the details of construction and the arrangement of components set forth in the following description or illustrated in the accompanying drawings. The present disclosure is capable of other embodiments and of being practiced or of being carried out in various ways.

Other aspects of the invention will become apparent by consideration of the detailed description and accompanying drawings.

DETAILED DESCRIPTION

Embodiments of the present disclosure relate generally to the genetic analysis of intractable microbes. More particularly, the present disclosure provides materials and methods that incorporate chemical mutagenesis, phenotypic selection, suppression analysis, and genomic sequencing-based mutational mapping, to identify novel genetic regulators in previously intractable organisms, such as microbes that constitute the human microbiome.

Microbial communities play important roles in human health. While DNA sequencing technologies enabled a broad assessment of microbial diversity and genomic content, the molecular mechanisms underlying microbe-microbe and microbe-host interactions are not yet well-defined, in part because only a small fraction of microbes are amenable to molecular genetic manipulation. Methods of the present disclosure are generally independent of recombinant DNA tools, and instead involve genetic analysis suitable for in any cultivatable microbial species. Methods of the present disclosure facilitate the identification of genetic determinants of various microbial traits important for host colonization (e.g., motility) in members of the vertebrate microbiome (e.g., Firmicutes *Exiguobacterium acetylicum*), and enable the experimental determination of the roles for such genetic determinants in host colonization.

A significant impediment to understanding how microbes in the gastrointestinal tract colonize and influence the physiology of their hosts is the challenges associated with genetic manipulation of intractable microbes. Embodiments of the present disclosure involve the application of population-based genomic sequencing after chemical mutagenesis to map bacterial genes responsible for motility in *Exiguobacterium acetylicum*, a representative intestinal Firmicutes bacterium that is intractable to molecular genetic manipulation. In accordance with these embodiments, significant associations between mutations in 57 *E. acetylicum* genes and impaired motility were established, and less than half of these genes were annotated or previously known to be important for motility-related functionality. The genetic link between individual mutations and loss of motility for several of these genes was determined by performing large-scale analysis of spontaneous suppressor mutations; several genes belonging to a broad family of diguanylate cyclases and phosphodiesterases were re-annotated to highlight their specific role in motility, and several other uncharacterized genes were assigned motility functions. Additionally, isogenic strains were generated that confirmed that *Exiguobacterium* motility is important for the colonization of its vertebrate host. Overall, the methods of the present disclosure indicate that genetic dissection of a complex trait (e.g., motility), functional annotation of new genetic regulators, and the generation of mutagen-induced variants can be coordinated to define the role for these genetic regulators in complex environments, such as the microbiota of the human gut.

Embodiments of the present disclosure include methods of identifying genetic regulators of a trait in a microbe affecting host colonization. In some embodiments, the methods of the present disclosure include exposing a microbe to a mutagen to produce a plurality of mutagenic variants, performing phenotype-based assessment of the mutagenic variants based on at least one trait, sequencing at least a portion of the plurality of mutagenic variants' genomes, and determining differences in the genomic sequences of the plurality of mutagenic variants as compared to a reference genome. In some embodiments, differences in the genomic sequences between the plurality of mutagenic variants and the reference genome can be indicative of a genetic regulator of the trait affecting host colonization.

In some embodiments, methods of the present disclosure include performing bioinformatics analysis to identify known genetic regulators of a trait, and determining differences between the sequences of the known genetic regulators and the genomic sequences of the plurality of mutagenic variants. Bioinformatics analysis can include the use of any type of computer-based program that facilitates the analysis of genomic information, including but not limited to, keyword searches, reciprocal BLAST homology searches, Pfam searches, and the like. Bioinformatics analysis can be used in conjunction with various sequencing methods and methods of sequence analysis, as would be recognized by one of ordinary skill in the art based on the present disclosure. For example, whole genome sequencing can be used to identify genetic regulators of a trait, and to determine mutagen-induced single nucleotide variants (SNVs) in the trait, based on a reference genome (e.g., non-mutagenized genome of an organism of the same species).

In some embodiments, methods of the present disclosure include performing suppression-based analysis of the plurality of mutagenic variants, including passaging one or more of the plurality of mutagenic variants and performing phenotype-based assessment of the one or more of the plurality of mutagenic variants to identify variants exhibiting the desired phenotype associated with the trait. Suppression-based analysis can include suppression screens in which mutagenic variants are identified by their ability to express an altered (e.g., reversal) phenotype, as compared to a previous phenotype (e.g., non-motility vs. motility). Suppression-based analysis can confirm the function of a particular genetic regulator, and can be used to facilitate the identification of new genetic regulators.

In accordance with these embodiments, genetic regulators (also referred to as genetic determinants) can include genome-based loci that influence a trait of a microbe. Genetic regulators can include genes and/or genetic regulatory elements that modulate the expression and/or function of other genes that can influence a trait. In some embodiments, genetic regulators are genes that have been previously identified or annotated as being capable of influencing a trait-of-interest or a plurality of traits-of-interest. In other embodiments, genetic regulators are genes that have not been previously shown to influence a trait-of-interest or a plurality of traits-of-interest, and therefore, these genetic regulators can represent novel targets for therapeutic intervention.

In some embodiments of the present disclosure, a trait of a microbe can be any characteristic that is genetically determined, including but not limited to, motility, amino acid biosynthesis, carbohydrate metabolism, nutrient uptake, redox tolerance, secretion, adherence, invasion, respiration, growth, reproduction, and the like. A trait(s) of a microbe can also be a characteristic that can be used as the basis for phenotypic analysis, such as a phenotypic screen used to identify genetic regulators of the trait(s). A trait can include a genetically-determined characteristic of a microbe that is important for the overall growth and survival of that microbe, such as the ability of the microbe to colonize a host. In some embodiments, a trait can include motility, such that genetic regulators of motility (e.g., flagellar assembly and/or function) can be altered in such a way as to reduce the motility of the microbe and hence reduce the ability of the microbe to colonize a host. In some embodiments, known genetic regulators of microbe motility can include fliE, fliF, fliK, figG1, flhA, fliM, flgN, and hag1. And in other embodiments, unknown and/or unannotated genetic regulators of microbe motility can include ftsX, ea2619, ea2862, and ea2157.

In accordance with embodiments of the present disclosure, mutagenic variants can include microbes that have been treated with a mutagen to induce mutations in the microbe's genome such that a mutagen-induced variant is obtained. Mutagenic variants can subsequently be subjected to phenotype-based analysis to identify genetic regulators of a particular trait. In some embodiments, the mutagen is a chemical mutagen, including but not limited to, ethyl methyl sulfonate (EMS), methyl methane sulphonate (MMS), nitrous acid, N-ethyl-N'-nitro-N-nitrosoguanidine (ENNG), 1,2-dibromoethane (DBE), 1-chloro-2,4-dinitrobenzene (CDNB), styrene-7,8-oxide (STOX), N-ethyl-N-nitrosourea (ENU), and the like. In other embodiments, the mutagen is radiation or ultraviolet light. Other mutagens can also be used with the methods of the present disclosure, as would be recognized by one of ordinary skill based on the present disclosure.

In accordance with embodiments of the present disclosure, a microbe can be a bacteria, including but not limited to, *Acidovorax, Acinetobacter, Agrobacterium, Akkermansia, Alistipes, Allobaculum, Aquabacterium, Azonexus, Bacillaceae* 1, *Bryantella, Carnobacteriaceae* 1, *Chryseobacterium, Chryseomonas, Cloacibacterium, Comamonas, Dechloromonas, Delftia, Enterobacter, Erwinia, Exiguobacterium, Flavimonas, Fusobacterium,* Gp1, Gp2, *Helicobacter, Lactobacillus, Lactococcus, Leuconostoc, Methylobacterium, Micrococcineae, Novosphingobium, Pantoea, Pseudomonas, Pseudoxanthomonas, Roseburia, Rubrobacterineae, Serratia, Shinella, Sphingobium, Staphylococcus, Stenotrophomonas, Succinivibrio, Sutterella, Syntrophococcus, Turicibacter, Variovorax*, and *Weissella*. In some embodiments, the bacteria are from the genus *Exiguobacterium*. Other microbes can also be used with the methods of the present disclosure, as would be recognized by one of ordinary skill based on the present disclosure. In some embodiments, the microbes are isolated from the microbiota of a human, such as gut microbiota. Such microbes can also be considered intractable in that they are difficult to characterize genetically and phenotypically due to their existence in a complex environment. Embodiments of the present disclosure are particularly suitable for use with microbes that are considered intractable.

Embodiments of the present disclosure also include methods for improving gut health in a subject, such as that of a human subject, by modulating one or more genetic regulators identified using the above-described methods. Such methods can include exposing a microbe known to be a part of the gut microbiota of a subject to a mutagen to produce a plurality of mutagenic variants, performing phenotype-based assessment of the mutagenic variants based on at least one trait, sequencing at least a portion of the plurality of mutagenic variants' genomes, and determining differences in the genomic sequences of the plurality of mutagenic variants as compared to a reference genome. In accordance with these methods, differences in the genomic sequences between the plurality of mutagenic variants and the reference genome can be indicative of a genetic regulator of the trait. In some embodiments, a subject can be treated with a therapeutic agent that modulates the expression and/or function of the genetic regulator of the trait, thereby improving gut health in the subject. Therapeutic agents can include polypeptides, nucleotides, small molecules, chemical compounds and the like. Therapeutic agents can be used to increase or decrease the expression and/or function of a genetic regulator to treat a condition in a human, depending on the underlying mechanism of action of the genetic regulator and its corresponding influence on a particular trait. In some embodiments, a therapeutic agent can be used to modulate the function of the genetic regulator in a manner that improves motility and enhances colonization of a microbe in the human gut.

Embodiments of the present disclosure can be used to develop broad methods for genetic analysis of "genetically intractable" microbes, by using *Exiguobacterium* sp as a representative gut microbe. A draft genome sequence of strain ZWU0009 (Taxonomy ID: 1224749) was generated. The ZWU0009 genome is ~3.2 Mb and includes 3289 CDS, 30 rRNA operons and 76 tRNAs. A comparative genome analysis indicated a close relationship with other previously characterized *Exiguobacterium* and that this isolate is a new variant of *E. acetylicum*. In some embodiments, whole genome sequencing can be used to monitor experimentally induced (e.g., mutagen-induced) genetic variations in *E. acetylicum* ZWU0009 and associations between mutagen-induced variants and phenotypically selected traits can be established, a process termed Mutational Enrichment Analysis after Phenotypic Selection (MEAPS) (FIG. 1A). MEAPS can be used to analyze any microbe, including determining the genetic regulators of *Exiguobacterium* motility, a multigenic complex trait that is important for some bacterial pathogens to colonize the vertebrate gut.

Figure 1B:
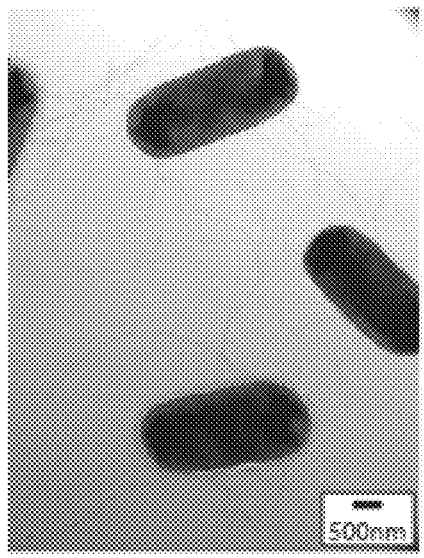

As would be recognized by one of ordinary skill in the art based on the present disclosure, the role of motility in host colonization by commensal bacteria is not well-defined; thus the materials and methods of the present disclosure fulfill a need for biological tools that can be used to determine these roles. Furthermore, metatranscriptomic analysis of healthy gut microbiotas indicates a broad dampening of the expression of motility genes in Firmicutes and *Proteobacteria* as a result of innate and adaptive immune responses, suggesting that the expression of flagella may confer a disadvantage to commensal bacteria. *E. acetylicum* expresses peritrichous flagella, as assessed by transmission electron microscopy (TEM), when grown in rich media (FIG. 1B), and therefore, the present disclosure includes the surprising finding that motility in general, including flagellar function, are important for microbe colonization of its host.

Figure 5:
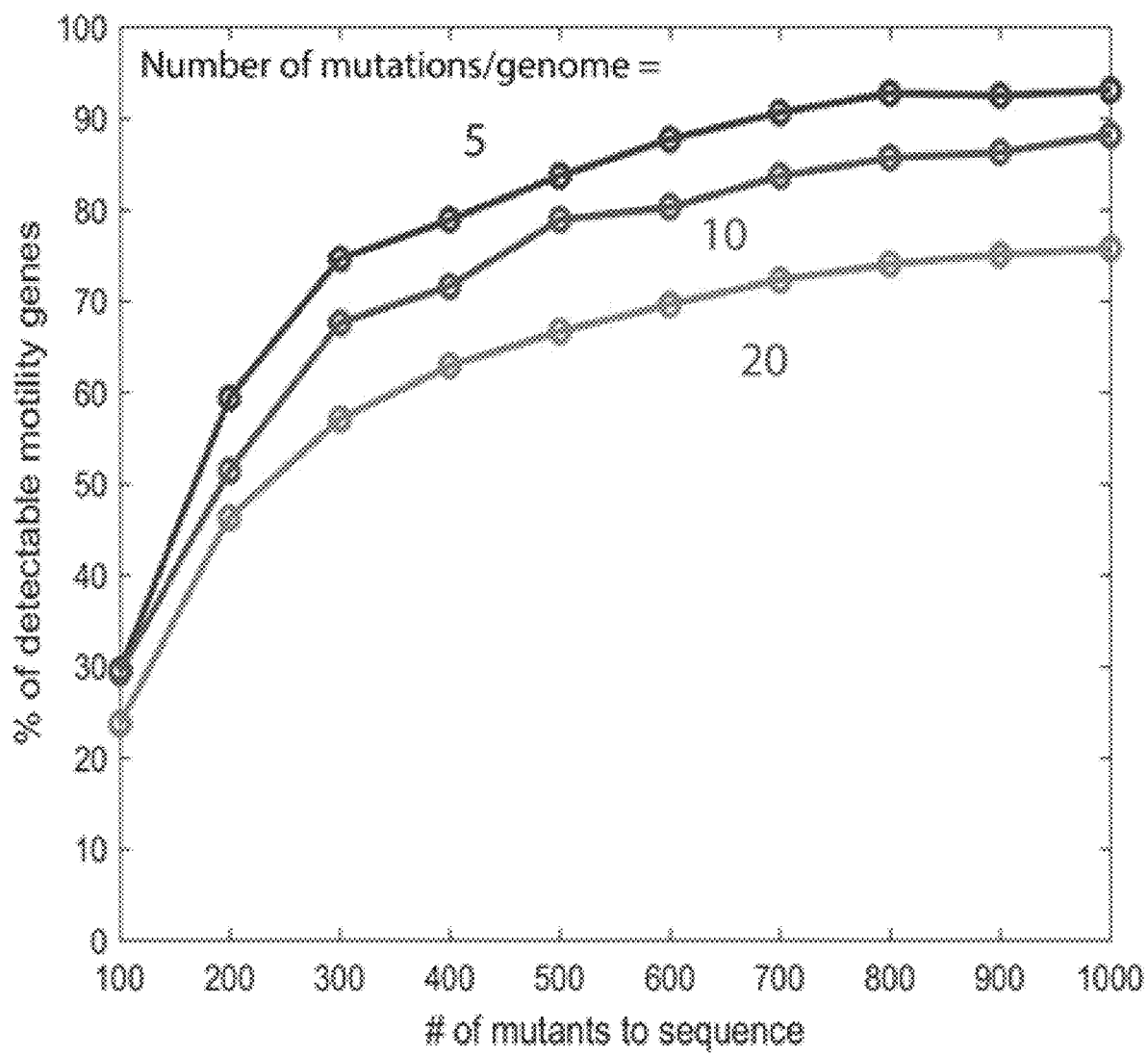
FIG. 5 is a representative line graph simulating the rate of identification of motility genes based on the sequencing of non-motile mutants.

In some embodiments, bioinformatics analysis such as keyword searches and reciprocal BLAST queries can be used to identify genetic regulators of traits important for microbe host colonization. For example, the present disclosure identified that 126 *E. acetylicum* genes are involved in motility (data not shown). To determine the number of non-motile *E. acetylicum* mutants, sequence analysis was used to identify mutations in overrepresented genes in motility loci, and initial MEAPS experiments were performed with the assumption that 100 genes are required for motility and each non-motile mutant had one motility-disabling mutation. These simulations indicated that by sequencing the genomes of 400-500 non-motile mutants with an average of 10 mutations/genome we can capture ~70% of all motility genes (FIG. 5). Further changes in the number of mutagenic variants sequenced or mutagenesis rates only led to marginal increases to the number of new motility genes that could be identified.

In accordance with embodiments of the present disclosure, mutagenic variants can be generated with various mutagenic agents, such as chemical mutagenic agents including but not limited to ethyl methyl sulfonate (EMS), methyl methane sulphonate (MMS), nitrous acid, N-ethyl-N'-nitro-N-nitrosoguanidine (ENNG), 1,2-dibromoethane (DBE), 1-chloro-2,4-dinitrobenzene (CDNB), styrene-7,8-oxide (STOX), and N-ethyl-N-nitrosourea (ENU). For example, *E. acetylicum* mutants can be generated by treatment with ethyl methyl sulfonate (EMS) and the ability of *E. acetylicum* to swarm in soft agar plates can be used to establish a phenotype-based assay for identifying non-motile mutants. In some embodiments, *E. acetylicum* inoculated in the center of a 0.3% agar plate will spread as large halos of turbidity emerging from the inoculation site. After at least three serial passages of pools of mutagenic variants in soft agar with repeated collection of bacteria from the site of inoculation, bacterial clones were tested for defects in swarming motility and stored them as individual clones (FIGS. 6A-6B).

In some embodiments, a sequencing pooling strategy can be used to aid in the determination of genetic regulators of a particular trait of interest. For example, pooling was used to sequence 440 non-motile *E. acetylicum* mutants and all the mutagen-induced single nucleotide variants (SNV) were identified by mapping unique sequence reads to a reference genome. To compensate for mutational biases due to gene length and relative % GC content, sequencing of 700 EMS-generated mutants that had not been selected for the loss of motility can also be performed. As discussed below, between about 4009 and about 5013 SNVs among the selected (non-motile) and unselected strains, respectively, were identified.

Figure 1C:
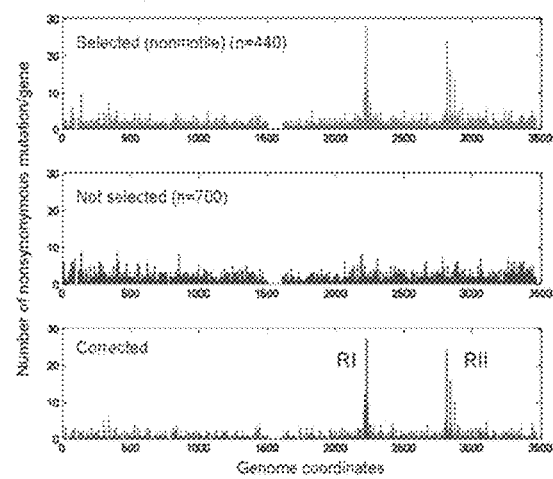
Figure 1E:
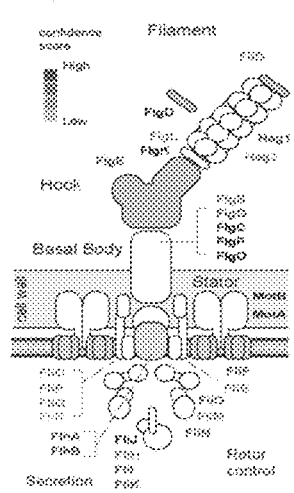
Figure 1D:
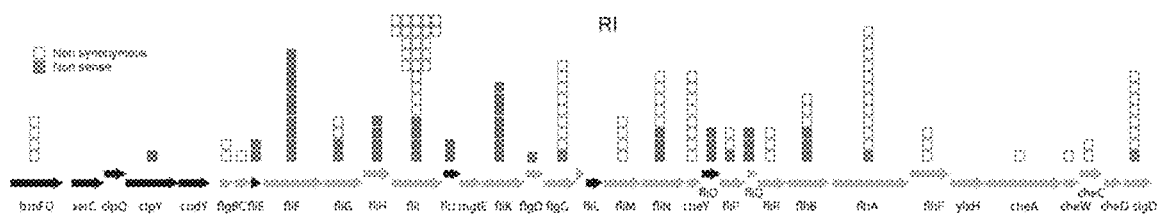
Figure 7:
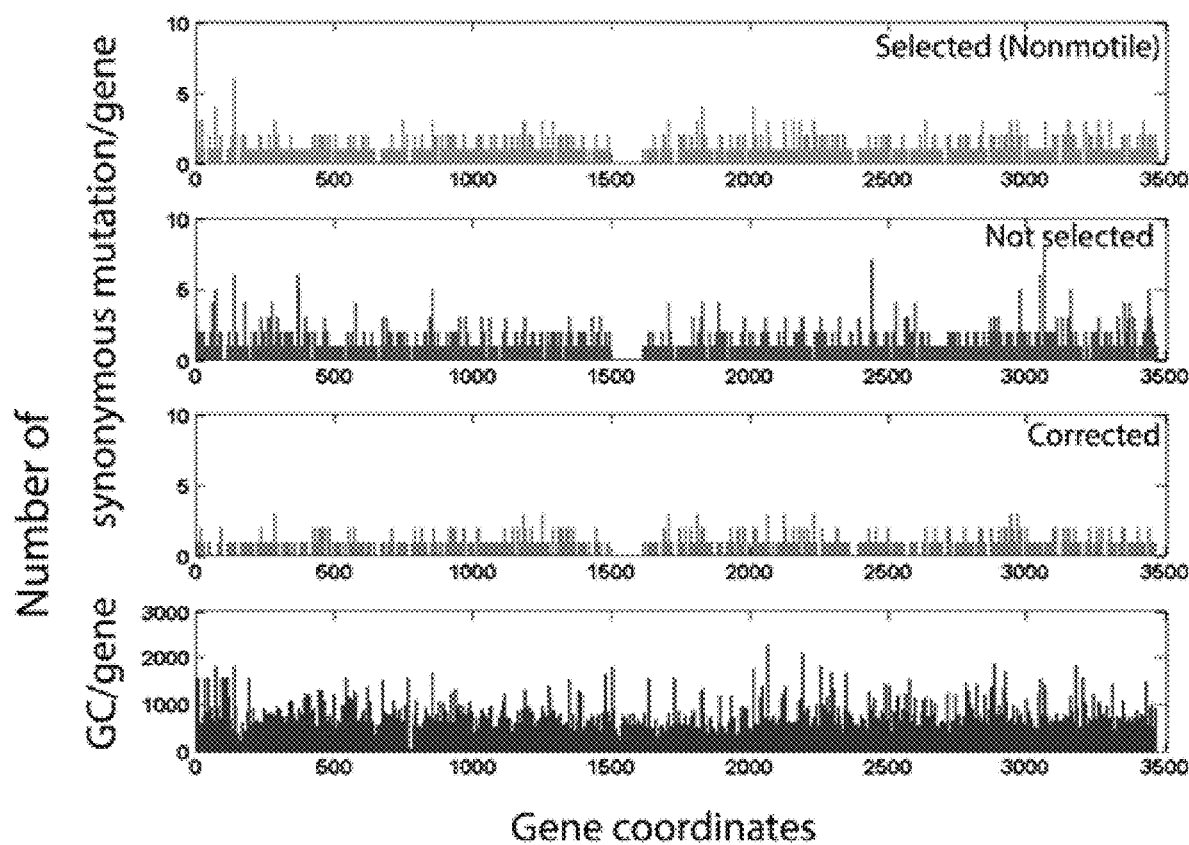
FIG. 7 is a representative image illustrating the location and abundance of synonymous mutations in E. acetylicum mutants that were selected or not selected based on motility was determined by sequencing the genomes of pools of mutants.

Mutation frequencies can then be compared between these sets of mutagenic variants and regions in the microbe's genome that display a marked accumulation of nonsynonymous, but not of synonymous, mutations can be identified (FIGS. 1C and FIG. 7). For example, region I of the *E. acetylicum* genome encompasses the most predicted flagellar structural genes and chemotaxis genes (FIG. 1D). Region II of the *E. acetylicum* genome encoded additional predicted flagellar structural components, including two flagellin (hag) genes, and the two component regulatory system, DegS/DegU. Using more stringent criteria (see Material and Methods), 57 genes were defined as most likely required for motility, including 27 genes homologous to genes not commonly associated with motility in Gram positive bacteria and 7 genes encoding proteins of unknown function. In general, genes with the highest confidence included 21 genes identified by MEAPS (FIG. 1E), which are homologous to genes previously associated with the assembly of flagella or the regulation of motility in bacteria. Overall, 102 genes were overrepresented among non-motile strains including 19% of genes identified as potential motility genes by key word searches.

Figure 2A:
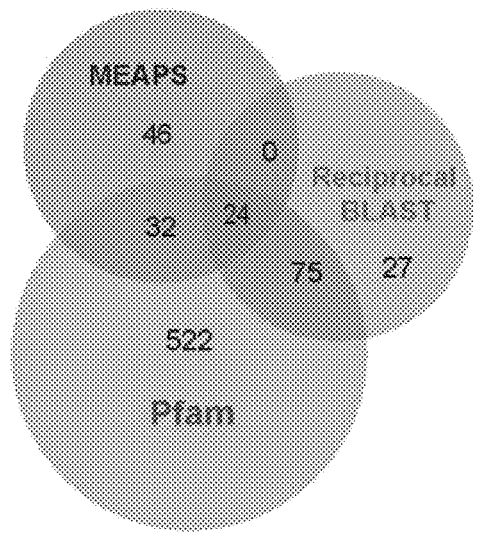
FIGS. 2A-2D include functional characterization of motility genes in *E. acetylicum* by reciprocal BLAST homology searches, Pfam terms associated with motility, and MEAPS analysis (A); suppression analysis of nonsense mutations in putative structural flagellar genes (B); representative transmission electron micrographs demonstrating that intragenic suppressor of a hag1 nonsense allele restores the formation of wild type flagellar structures in *E. acetylicum* (C); and representative bar graphs demonstrating that motility enhances *E. acetylicum* colonization of germ free zebrafish in vivo (D).

These results demonstrate the surprising result that the majority of genes predicted by bioinformatics analysis to participate in *E. acetylicum* motility do not play a role in motility under the conditions tested (FIG. 2A). Intergenic regions (FIG. 8) were also monitored and mutations were identified in three loci that were overrepresented in non-motile mutants, including SNVs mapping to the predicted ribosome-binding site of cheY and flhA, encoding putative chemotaxis and flagellar structural proteins, respectively.

Figure 2C:
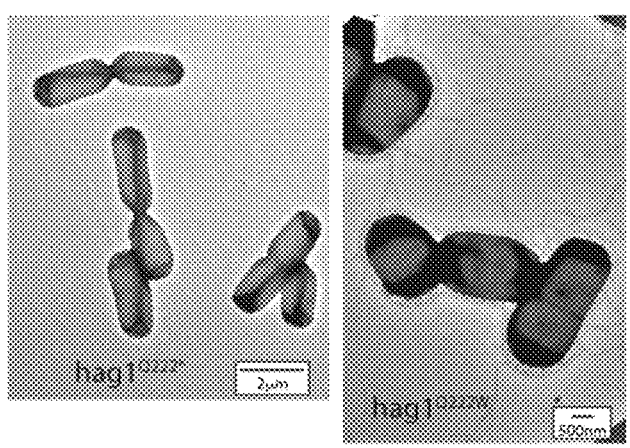

Although MEAPS methodology as described in the present disclosure can be used to identify significant associations between mutations in specific genetic regulators of important host colonization traits (e.g., motility), additional methodology can be used to isolate spontaneous genetic suppressors of mutations in the mutagenic variants, and to determine if the genetic regulators identified demonstrate a mechanistic correlation to the trait. In some embodiments of the present disclosure, mutagenic variants were isolated strains from those with nonsense mutations in flhA, which is required for flagellar biosynthesis; fliE, fliF, fliK and flgG1, which encode core components of the basal structure; fliM, which encoded the flagellar M-ring and switch component; flgN, which encodes a secretion chaperone; and hag1, which encodes one of the two predicted flagellin subunits. Mutants were passaged on soft agar plates and bacteria were collected from the leading edge of the inoculation spot. After 3-4 passages, clonal populations of strains that had regained motility were isolated and the DNA region spanning the predicted motility gene was sequenced. In all instances, suppressor mutations either reversed the original nonsense mutation or changed adjacent nucleotides to generate a reading codon (FIG. 2B), indicating that for loss-of-function mutations in predicted structural flagellar genes and accessory factor(s), restoring motility includes repairing the nonsense mutation. In a representative hag1 nonsense mutant, flagella were observed by TEM only after intragenic repair of the nonsense lesion to generate a Q to W codon switch (FIG. 2C). These findings provide compelling genetic evidence that the mutations identified by MEAPS methodology of the present disclosure were responsible for the loss of motility.

Figure 2B:
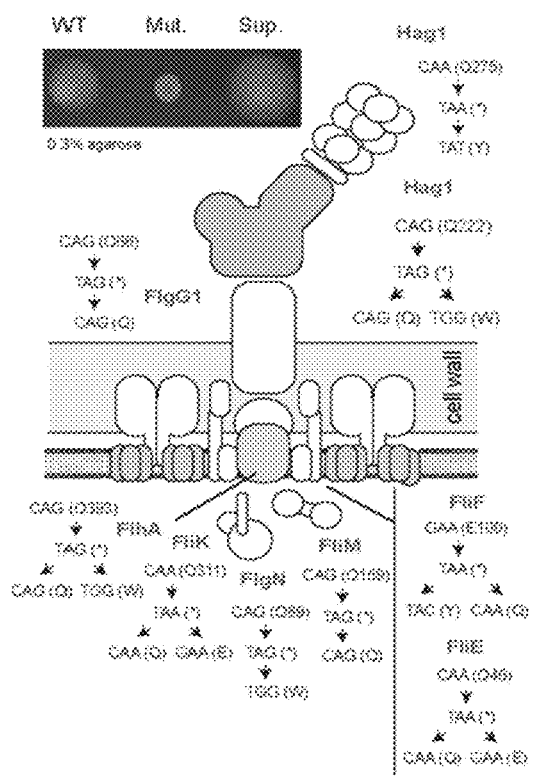
Figure 2D:
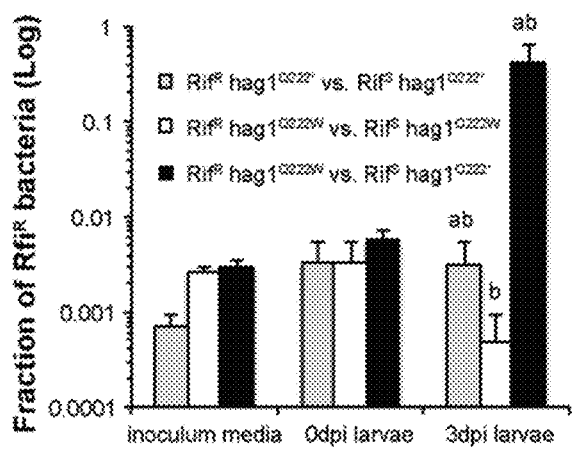

The availability of genetically defined non-motile and co-isogenic suppressor strains of mutagenic variants enables the determination of whether flagellar motility is required for *E. acetylicum* host colonization in vivo, such as in the zebrafish model system. For example, rifampin resistant variants of a strain bearing a hag1 (ea2793) nonsense mutation (Hag1Q222*) were isolated along with its suppressed sister strain (Hag1 Q222W) and competitive colonization experiments were performed in germ-free zebrafish larvae. The relative enrichment of one strain over the other at 3 days post inoculation was then assessed by plating larvae-associated bacteria and enumerating rifampin resistant colonies. The non-motile hag1 mutagenic variants were rapidly outcompeted by their motile suppressors even when the majority of the starting inoculum consisted of non-motile strains (FIG. 2D). Similar results were obtained with a competition between a spontaneous flhA mutant (data not shown) and a wild type strain (FIG. 9), confirming the role for motility in stable colonization of its vertebrate host.

Figure 3A:
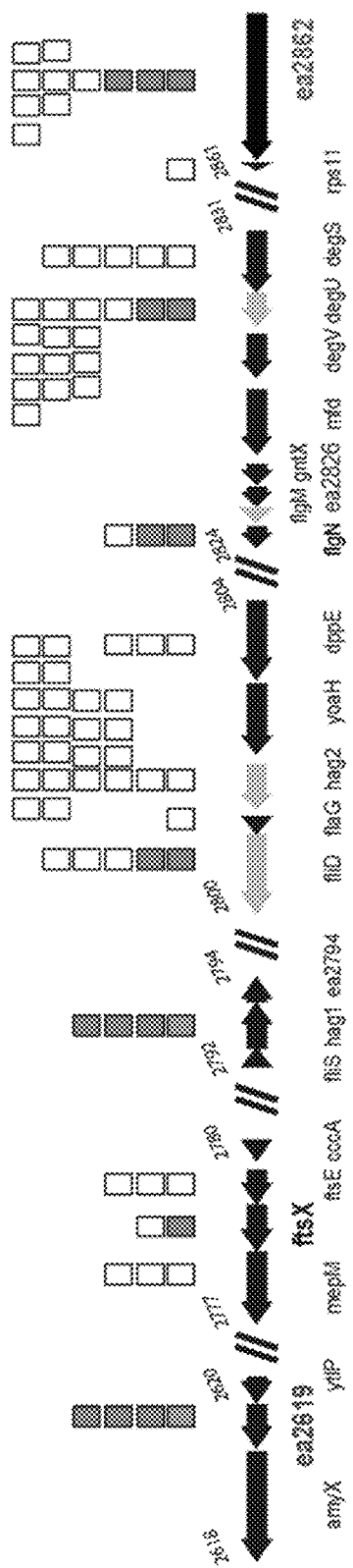
FIGS. 3A-3C include a representative schematic indicating that motility Region II of *E. acetylicum* encodes for new motility genes (A); a representative schematic indicating that non-synonymous mutations in uncharacterized genes and close homologues of predicted motility genes (light arrows) in the RII motility region are overrepresented among non-motile *E. acetylicum* mutants (B); and representative transmission electron micrographs demonstrating motility behavior and flagellar assembly of a FtsXQ82* nonsense *E. acetylicum* mutant and a spontaneous variant that regained motility (FtsXQ82W) (D).
Figure 3B:
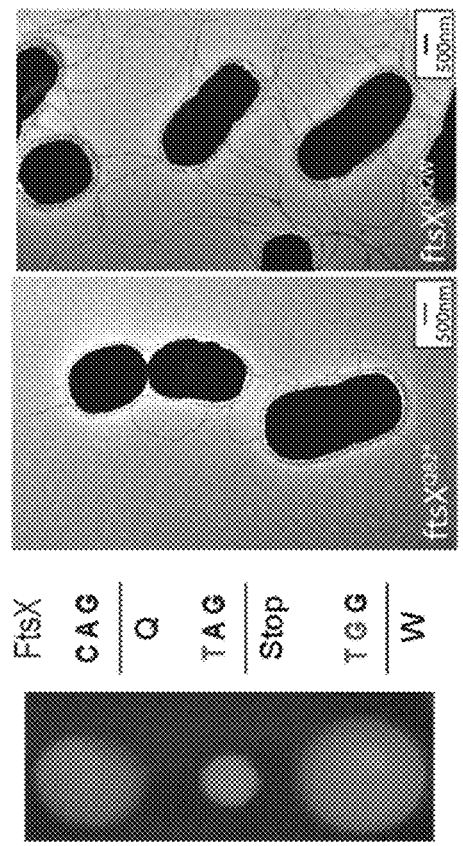
Figure 3C:
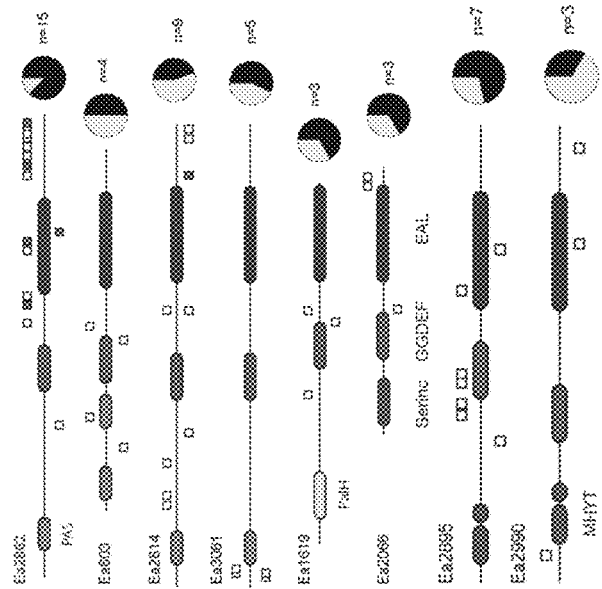

Genetic suppression analysis can also be used to define the role of genetic regulators annotated with ambiguous or unknown functions. For example, genetic suppression analysis was used to define the role of genetic regulators annotated with ambiguous or unknown functions, which were identified as motility genes using MEAPS methodology. Suppressors of nonsense alleles of uncharacterized genes in region II included: ea2862, encoding a protein with domains with predicted diguanylate cyclase (GGDEF; SEQ ID NO:1) and phosphodiesterase activities (EAL; SEQ ID NO:2), respectively; ea2619, encoding a hypothetical protein; and ftsX, encoding a protein associated with septation and sporulation (FIG. 3A). GGDEF/EAL domain proteins regulate the formation of c-di-GMP, a signaling molecule that controls multiple cellular behaviors including motility and biofilm formation. The *E. acetylicum* genome encodes ten proteins with tandem GGDEF/EAL domains, but only two genes encoding GGDEF/EAL proteins displayed a significantly higher mutational load among non-motile mutants (FIG. 3B). For the ftsX nonsense mutant, as with structural flagellar genes, the suppressor mutations isolated were intragenic and consisted of reversions of the original mutation or nucleotide changes that restored translation (FIG. 3C). In *B. subtilis*, the FtsXE complex is required for the secretion of peptidoglycan hydrolases CwlO and LytE and proper septum assembly during sporulation and elongation, and peptidoglycan remodeling is important for flagellar biosynthesis and function in Gram positive bacteria. Interestingly, although FtsX in *B. subtilis* and *E. acetylicum* are 49% identical and share similar chromosomal location adjacent to motility genes, FtsX has not previously been associated with motility in *B. subtilis*. Flagella were readily apparent in ftsX mutants indicating that CwlO, LytE, and related peptidoglycan remodeling enzymes are not required for flagellar assembly (FIG. 3D).

Figure 4A:
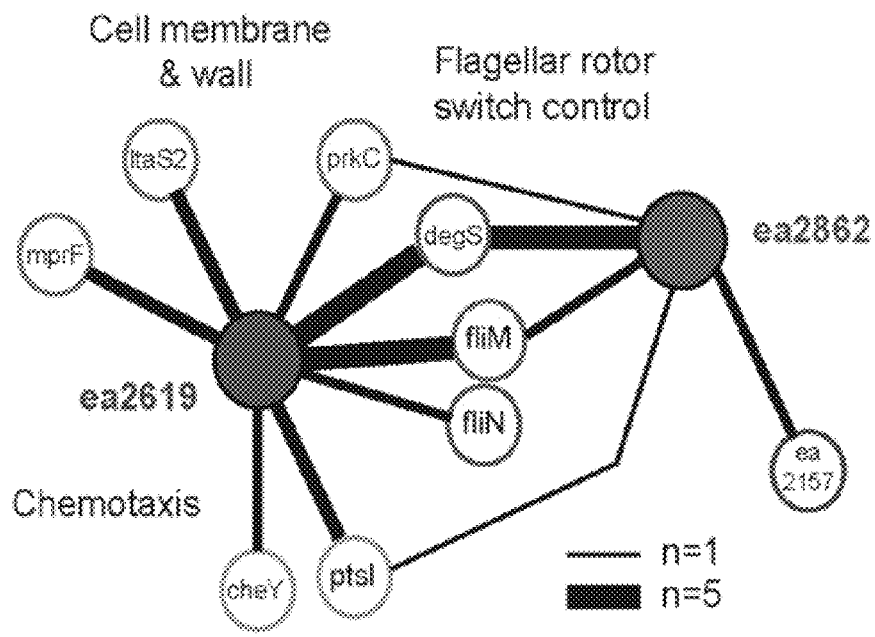
FIGS. 4A-4B include a representative schematic illustrating that extragenic suppression analysis of non-motile *E. acetylicum* mutagenic variants identifies a role for cell wall modifications and c-di-GMP sensing in commensal Firmicutes motility (A); and a representative schematic illustrating that suppression analysis of loss of function alleles in two novel motility genes indicates that loss of motility in mutants defective for ea2619 and ea2862 can be bypassed by changes in flagellar rotor switch control and chemotaxis (B).
Figure 4B:
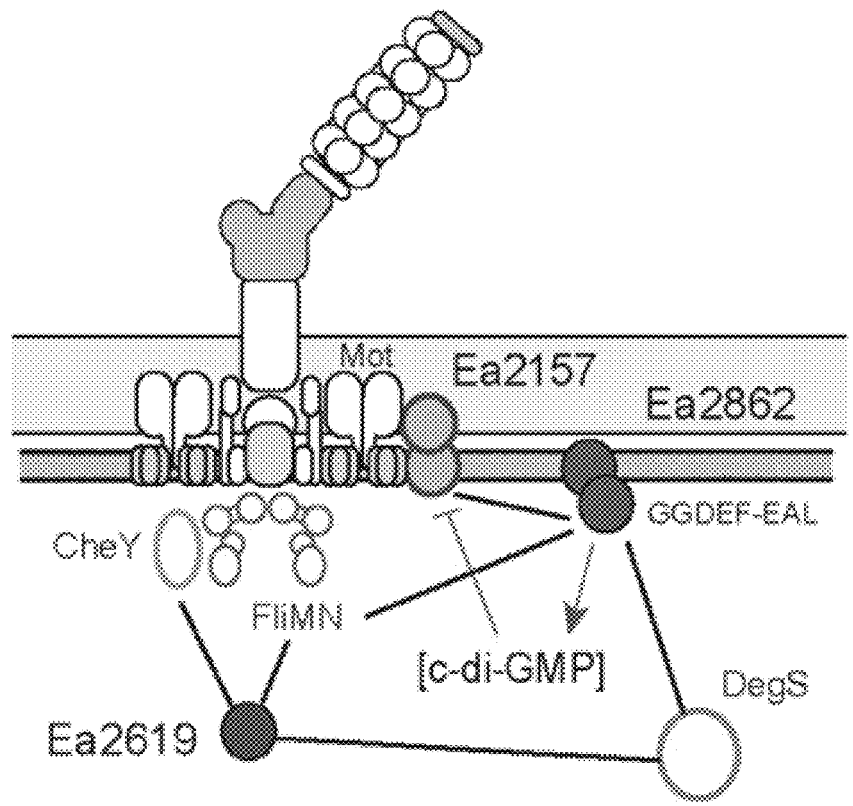

For nonsense mutations in ea2862 and ea2619, multiple extragenic suppressor mutations were identified that restored motility. Common suppressor mutations of at least three independent nonsense alleles of ea2862 and of ea2619 included point mutations in the flagellar switch proteins FliM and FliN, regulators of chemotaxis (CheY and PtsI), and the kinase DegS (24) (FIG. 4A). Mutations in these genes were also common in spontaneous *E. acetylicum* mutant strains that had been selected for hypermotility on soft agar. Overall, these data indicate that mutations in ea2862 and ea2619 likely regulate the frequency and direction of motility as opposed to flagellar assembly or function.

EXAMPLES

The following examples are illustrative of disclosed methods. In light of the present disclosure, those of skill in the art will recognize that variations of these examples and other examples of the disclosed method would be possible without undue experimentation.

Example 1 Identification of Genes Required for Motility in *E. acetylicum*

FIG. 1 includes a representative schematic of the materials and methods of the present disclosure, which can be used to incorporate chemical mutagenesis and DNA sequencing to perform a mutational enrichment analysis after phenotypic selection (MEAPS) and identify genes required for swarming motility (FIG. 1A). Representative transmission electron micrographs of *E. acetylicum* flagella are also shown (FIG. 1B; bar: 0.5 µM). The MEAPS methodology of the present disclosure enabled the identification of *E. acetylicum* strains defective for motility (FIG. 1C). *E. acetylicum* mutants, or mutagenic variants, were selected based on the loss of swarming (n=440) or not selected (n=700) and their genomes sequenced. The normalized frequency of nonsynonymous mutations reveals two chromosomal regions (RI and RII) that preferentially accumulate mutations in non-motile *E. acetylicum* strains. Peaks highlight predicted motility genes based on their similarities to motility genes in other bacteria. Bars represent genes annotated as motility-related genes. Genetic mapping of ORFs in motility Region I are shown in FIG. 1D. Genes with homology to predicted motility genes are shown as light arrows and the number of nonsense and non-synonymous mutations identified, after correction, is represented by gray and white squares, respectively. FIG. 1E includes a representative schematic of the Gram positive flagellar apparatus displaying all components conserved in *E. acetylicum*. Components identified by MEAPS are shown in different font colors to reflect confidence of their relative association with motility.

Example 2: Functional Characterization of Motility Genes in *E. acetylicum*

FIG. 2A illustrates an overlapping set of putative *E. acetylicum* motility genes identified either by reciprocal BLAST homology searches, Pfam terms associated motility, and MEAPS. FIG. 2B illustrates that suppressors of nonsense mutations in putative structural flagellar genes confirm their role in motility. Strains with nonsense mutations in flagellar components were passaged in soft agar to enrich for spontaneous motile variants (Inset: HagQ222* and its HagQ222W suppressor). Sequence analysis indicated the presence of reversions and intragenic suppressor mutations that restored the reading frame. The relevant sequence of mutated and suppressed codons is shown. As shown in FIG. 1C, an intragenic suppressor of a hag1 nonsense allele restores the formation of wild type flagellar structures in *E. acetylicum*. FIG. 2D indicates that motility enhances *E. acetylicum* colonization of germ free zebrafish. Rifampin (Rif) resistant and sensitive versions of an *E. acetylicum* strain with a nonsense mutation in Hag1 (Hag1Q222*) and its motile suppressor congenic sibling (Hag1Q222W) were placed in direct competition for colonization of 6 days post-fertilization germ free zebrafish embryos. The relative frequency of each strain in the inoculum media at 6 days post-fertilization and in association with animals 3 days post-inoculation (d.p.i.) was determined by assessing the percentage of Rif resistant bacteria. Error bars represent standard error of mean.

Example 3: Motility Region II of *E. acetylicum* Encodes for New Motility Genes FIG. 3A is a schematic representation illustrating that non-synonymous mutations in uncharacterized genes and close homologues of predicted motility genes (light arrows) in the RII motility region are overrepresented among non-motile *E. acetylicum mutants*. The number of independent nonsense and non-synonymous mutations identified is represented by gray and white squares, respectively. FIG. 3B demonstrates the identification of GGDEF/EAL domain-containing proteins in *E. acetylicum*. Only genes with more than 3 total non-synonymous mutations are shown. Pie charts indicate the proportion of total mutations identified among non-motile (black) and unselected (grey) mutant pools. Squares on top and bottom of each gene represent the location of mutations identified in the selected (non-motile) and unselected group, respectively. GGDEF (SEQ ID NO:1), diaguanylate cyclase domain; EAL (SEQ ID NO:2), phosphodiesterase domain; PAS (SEQ ID NO:3), sensor for signal transduction; MYHT (SEQ ID NO:4), bacterial signaling (Pfam03707); Serinc, serine incorporator (pfam03348); PalC, proteolytic processing (pfam08733). FIG. 3C demonstrates the trait of motility behavior and flagellar assembly of a FtsXQ82* nonsense *E. acetylicum* mutant and a spontaneous variant that regained motility (FtsXQ82W). TEM analysis of mutants and their suppressor indicate that FtsX is not required for flagellar assembly.

Example 4

Extragenic suppression analysis of non-motile *E. acetylicum* mutants identifies a role for cell wall modifications and c-di-GMP sensing in commensal Firmicutes motility. FIG. 4A is a representative schematic depicting the genetic suppressors of loss of function alleles in two novel motility genes indicates that loss of motility in mutants defective for ea2619 and ea2862 can be bypassed by changes in flagellar rotor switch control and chemotaxis. Motile variants of mutants bearing independent nonsense alleles of ea2619 or ea2862 were isolated. Common suppressor mutations (open circles) mapped to chemotaxis genes (brown), rotor control genes (green), regulators of flagellar gene transcription (blue), and cell membrane homeostasis (orange). Thickness of lines connecting nodes is proportional to the number of independent suppressor mutations identified. FIG. 4B is a representative schematic of suppressor mutations linking Ea2619 and Ea2862 to the regulation of swimming speed and direction. Ea2157 is a direct link to the levels of c-di-GMP regulated by Ea2862, and is important for the control of flagellar motility in *E. acetylicum* (arrow). Ea2157 was independently identified by MEAPS as a putative motility gene.

Example 5: Simulations of the Rate of Identification of Motility Genes Based on the Sequencing of Non-Motile Mutants As shown in FIG. 5, mutations in the *E. acetylicum* genome were generated in silico at random GC base pairs.

The mutagenesis rates were altered to generate 5, 10 or 20 mutations per genome (numbers next to corresponding line on graph), with the assumption that only one mutation was responsible for the loss of motility. The number of "motility" genes was fixed at 100. The simulations indicated that at an average of 10 mutation/genome, sequencing of 400-500 non-motile mutants can lead to the identification of 70-75% of motility genes based on their high frequency of accumulation of nonsynonymous mutations.

Example 6: Isolation of Non-Motile *E. acetylicum* Mutants

As shown in FIG. 6A, chemically mutagenized bacteria were inoculated on 0.3% agar plates to enrich for non-motile strains based on their inability to migrate away from the inoculation site. After 3-4 passages, individual clones were derived from bacteria that remained near the inoculation site and individually tested in a 96 well plate format. Each clone was inoculated at the edge of the well and incubated for 24 h. Motile strains covered the entire well and appeared turbid. Strains impaired for motility remained near the edge. FIG. 6B is a representative image of a 96 well plate used to screen for motility defects. Candidate non-motile mutants are indicated with arrows. As shown in FIG. 6C, secondary confirmation tests for the loss of motility were conducted. Saturated bacterial cultures were inoculated in the middle of 0.3% agar in 24 well plates and incubated for 24 h. The relative diameter of the bacterial colony was used as criteria to identify mutants with significant defects in swarming motility.

Example 7: the Location and Abundance of Synonymous Mutations in *E. acetylicum* Mutants that were Selected or not Selected Based on Motility was Determined by Sequencing the Genomes of Pools of Mutants As shown in FIG. 7, the corrected frequency of synonymous mutations in non-motile *E. acetylicum* mutants reveals no clear bias in mutations in any particular locus. The number of GC bases per gene (bottom panel) indicates the likelihood of mutational biases based solely on targets for EMS mutagenesis. (The regions between 1500-1600 were omitted from analysis as this region contains rDNA and other repetitive regions that confound alignment of sequencing reads to a unique locus.)

Example 8: Comparative Analysis of Mutations in Noncoding Regions

Figure 8:
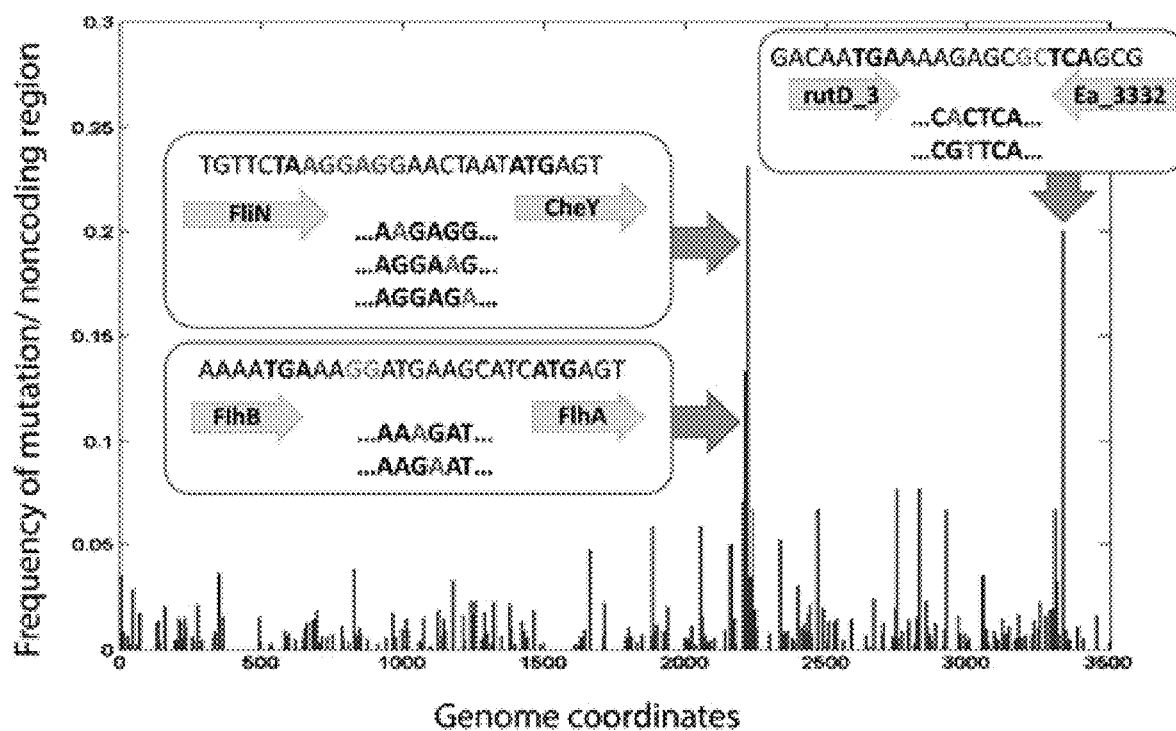
FIG. 8 is a representative image illustrating the distribution of single nucleotide variants (SNVs) in non-coding regions of E. acetylicum mutants that had been selected based on their motility.

FIG. 8 illustrates the distribution of single nucleotide variants (SNVs) in non-coding regions of *E. acetylicum* mutants that had been selected based on their motility. The frequency of mutation was normalized to the number of nucleotides in the non-coding region after correcting for mutation biases. In the regions exhibiting abnormally high frequencies of mutations, the nucleotide variants mapped to predicted ribosome sites of cheY (SEQ ID NO:5) and flhA (SEQ ID NO:6) respectively. The consequence of mutations in the intergenic region between rutD3 and ea3382 (SEQ ID NO:7) on motility is currently unknown since these genes do not appear to be directly involved in motility.

Example 9: Motility Contributes to the Efficient Colonization of Zebrafish by *E. acetylicum*

Figure 9:
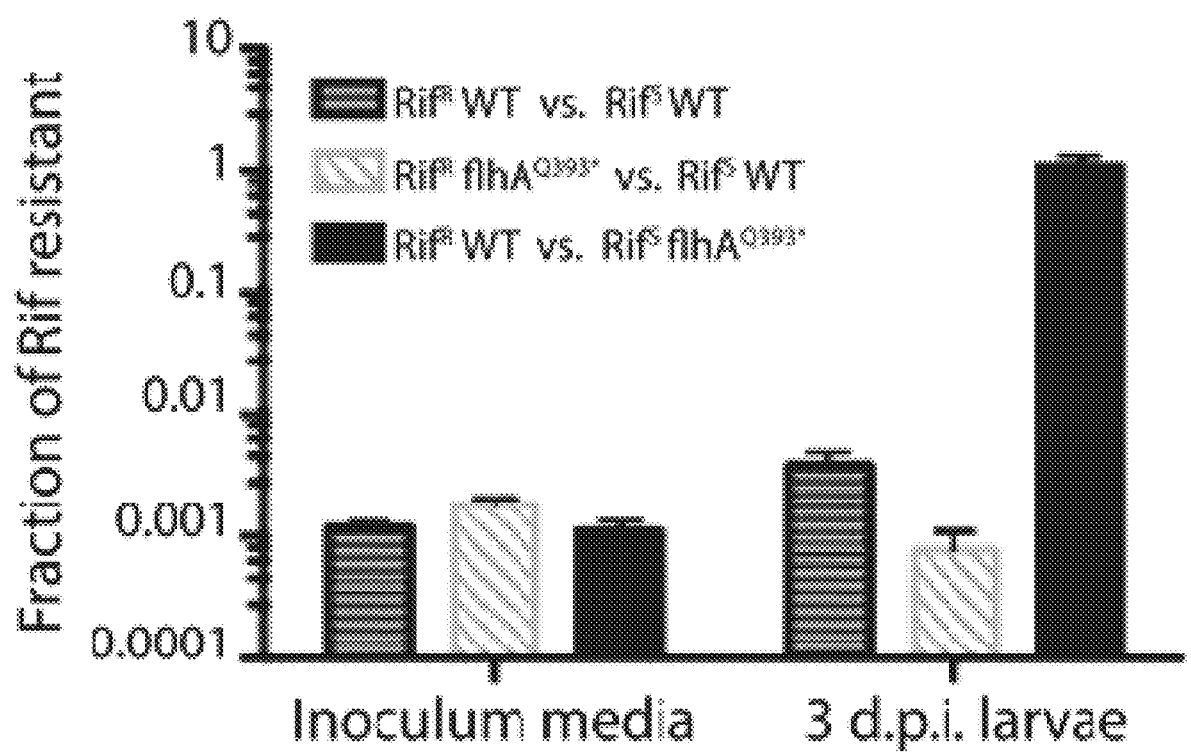
FIG. 9 is representative bar graph illustrating that motility contributes to the efficient colonization of zebrafish by E. acetylicum in vivo.

As shown in FIG. 9, rifampin (Rif) resistant and sensitive versions of an *E. acetylicum* strain with a nonsense mutation in flagellar biosynthesis gene, flhA, (FlhAQ393*) and wild type strain were placed in direct competition for colonization of 6 days post-fertilization germ free zebrafish embryos. The relative frequency of each strain in the inoculum media at 6 days post-fertilization and in association with animals 3 days post-inoculation (d.p.i.) was determined by assessing the number of rifampin resistant bacteria over total colony forming units. Error bars represent the standard error of mean (SEM).

Materials and Methods

De Novo Assembly and Gene Annotation of *E. acetylicum*.

*Exiguobacterium* sp. strain ZWU0009 (also referred to as ZF1EB02) was grown in Brain Heart Infusion (BHI) broth (BD Biosciences) overnight at 30° C. under aerobic conditions, and genomic DNA was isolated with a DNeasy blood and tissue kit (QIAGEN). PacBio RS (PACIFIC BIOSCIENCES INC.) library preparation and sequencing was performed at the Duke Sequencing and Genomic Technologies Shared Resource. PacBio reads were quality filtered and assembled with PacBio SMRT analysis software, using the HGAP2 protocol. The assembly resulted in circular contigs for the bacterial chromosome and four plasmids, and overlapping ends were trimmed. Subsequent gene annotation was performed with PROKKA. A complete, annotated genome and its analysis will be published separately. The Genbank accession number is GCA_000798945.1. Preliminary phlylogenetic analysis based on whole genome sequences indicate that *Exiguobacterium* sp. strain ZWU0009 is a variant of *Exiguobacterium acetylicum*.

Prediction of Motility Genes.

To identify genes with a potential role in motility, a keyword-search was performed of the NCBI refseq protein database (ncbi.nlm.nih.gov/refseq/) using the terms 'firmicutes' and 'motility'. Redundancies in the retrieved set of 36769 protein sequences were removed by clustering with USEARCH8 (drive5.com/usearch/), and output centroids were used as a database for reciprocal BLAST queries with predicted *Exiguobacterium* sp. ZWU0009 protein models. This analysis led to the identification of 126 potential motility genes. A separate bioinformatics search based on Pfam domains in the EMBL-EBI database (pfam.xfam.org/) using the keywords 'motility', 'flagellar' and chemotaxis' yielded 709 unique domains, which matched to 653 predicted *E. acetylicum* genes. Approximately 9% of these genes (56/653) were among the 102 putative motility genes identified by MEAPS.

Chemical Mutagenesis and Screening for Nonmotile *Exiguobacterium* Mutants.

*E. acetylicum* was mutagenized with 2.5-20 mg/mL EMS or N-ethyl-N-nitrosourea (ENU) (SIGMA-ALDRICH) in PBS for 1 h. Mutant bacteria were inoculated in 0.3% BHI agar plates. After overnight incubation, bacteria at the initial site of inoculation were collected and reinoculated in the center of another 0.3% agar plate to enrich for nonswarming mutants. After three rounds of enrichment, individual bacterial colonies were tested in a 96-well plating assay to identify mutants that failed to swarm in low-percentage agar.

Electron Microscopy Analysis of Flagellar. *E. acetylicum* wild-type, non-motile strains, and its suppressor strains were grown in brain heart infusion (BHI) medium at 30° C. Midlog bacteria were sedimented at 2000 rpm in a microcentrifuge and the bacterial pellet washed with PBS three times. The pellet was resuspended in PBS and applied onto a EM grid for one minute followed rinsed with water three times. Bacterial cells on the grid were fixed stained with 2% uranyl acetate and imaged using a Philips CM10 transmission electron microscope.

Screening for Non-Motile *Exiguobacterium* Mutants.

To select for non-motile mutants, EMS or ENU-treated *E. acetylicum* strains were streaked on the center of BHI plates made with 0.3% agar. After overnight incubation at 30° C., bacteria at the initial site of inoculation were collected and re-inoculated in the center of another 0.3% agar plate to enrich for non-swarming mutants. After three rounds of enrichment, individual bacterial colonies were tested in a 96-well plating assay to identify mutants that failed to swarm in low percentage agar. Transparent wells contained non-motile mutants whose growth was restricted to the site of inoculation, whereas uniformly cloudy wells contained motile mutants that swarmed across the entire well.

Computational Modeling.

A computational model was developed to predict what fraction of motility genes could be identified as a function of the number of non-motile mutants. The model simulated the genomic distribution of point mutations in non-motile mutant strains, with simulated loads of 5, 10, and 20 mutations per mutant strain. Genes were mutated at random, with the likelihood of mutation proportional to the number of G:C base pairs (the target of EMS and ENU) in each gene. Mutations were randomly generated as nonsynonymous, synonymous, or non-coding regions with a probability of 0.6, 0.3, and 0.1 respectively, based on our observation of rates in pilot experiments. Two simplifying assumptions were made in developing the model: i) there are 100 genes in *E. acetylicum* that are essential for motility, which is consistent with what is found in other bacterial species; and ii) for each non-motile strain a single mutation is assumed to be responsible for the loss-of-motility and all other mutations are assumed to have no phenotypic consequence. Genes were ranked by the number of nonsynonymous mutations observed in the simulation run, and a motility gene discovery rate was calculated as the fraction of genes labeled as motility genes that ranked in the top 3%. A final average motility gene discovery rate is the result from 1,000 simulations. Simulations were performed with MATLAB R2012a (MATHWORKS).

Genomic Sequencing of *E. acetylicum* Mutants.

*E. acetylicum* strains were cultured in BHI broth overnight at 30° C., and genomic DNA isolated with a DNeasy blood and tissue kit (QIAGEN). Pools were assembled consisting of 2.5 ng of total DNA isolated from each of 20 individual strains and a pre-sequenced mutant strain. Sequencing libraries were prepared and barcoded with a Nextera DNA library preparation kit (ILLUMINA) or NEBNext ultra DNA library prep kit (NEW ENGLAND BIOLABS), as recommended by the manufacturers. Five barcoded pools totaling 100 *E. acetylicum* strains were sequenced as single 50 base pairs reads on either a HiSeq2000 or HiSeq2500 sequencing platform (ILLUMINA). Duplicated reads from raw sequence reads were removed using VSEARCH (github.com/torognes/vsearch). Unique sequence reads derived from the mutagenized strains were mapped against the reference genome with Bowtie2. To identify single nucleotide variants (SNVs) among complex pools of mutants, SNVer (single nucleotide variant caller) was used. The Bonferroni method that SNVer uses for multiple-comparison corrections was omitted, and instead used a false discovery rate estimation to adjust raw p-value outputs from SNVer. The false discovery rate was set to 5%.

Mutational Enrichment Analysis.

The number of synonymous, nonsynonymous and nonsense mutations were determined for each gene for both the selected and unselected mutant pools. The unselected pool was used as background correction for biases in mutational frequency associated with the particulars of the *E. acetylicum* genome (e.g., GC content, mutational hotspots) by subtracting the number of mutations per gene found in the unselected pool from the selected pool. The number of nonsynonymous mutations per gene after correction was used to generate a rank order list of genes potentially required for motility. A cutoff point for putative motility genes was determined by the number of independent mutational events expected to have led to a loss of motility (n=440 for the total number of non-motile mutants isolated and the assumption that there is one causal mutation per mutant). Genes (n=37) with a net overrepresentation of 4 or more nonsynonymous mutations in the non-motile group accounted for ~60% of the expected mutational events. If a cutoff point of 3 or more nonsynonymous mutations is used, the list of genes increased to 88 and accounted for 92% of expected mutational events.

Two additional criteria were used to generate a "confidence score" that further sub classified these 88 putative motility genes. First, the distribution of synonymous and nonsynonymous mutations per gene was used to perform a Fisher's exact test to assess the probability that the spectrum of synonymous vs. nonsynonymous mutations deviates from a random distribution. Prior to performing Fisher's exact tests, the data was pre-filtered to remove genes that have zero or 1 nonsynonymous mutation from the unselected group. The Fisher's exact test was applied to the number of synonymous and nonsynonymous mutations identified for each gene in the selected and the unselected groups, and the number of non-mutagenized GC bases within each gene. The low frequency of mutational events per gene results in very few genes achieving significant p-values, but nonetheless provides a standardized means of generating a likelihood rank.

As a complementary approach, the frequency of nonsense mutations only was monitored, as they are the most likely ones to lead to a loss of function. The number of nonsense mutations per gene among non-motile mutants was determined, divided them by the potential number of codons in that gene that could be switched to a nonsense codon by a single EMS mutational event, and that number was used to rank these genes. This added an additional 14 genes that had been excluded from the preliminary list based on Fisher's exact test. Some of these include small genes with high homology to motility genes, but which had been excluded because of they had very few nonsynonymous mutations.

Next, the combined list of potential motility genes (n=102) was ranked by their Fisher's exact test p-value and their normalized frequency of nonsense mutations, and assigned each gene an arbitrary score (scale: 5 to 1) to reflect their relative rank. For instance, for nonsense mutations, arbitrary scores were given to genes in the top 10, 20, 30 or 40 percentile of the normalized frequency of nonsense mutation (only 40 genes out of 102 genes had nonsense mutations). For genes ranked by their Fisher's exact test p-values, arbitrary scores of 5-1 were given to genes in the top 10, 25, 45, or 75 percentile. Finally, an overall score was then determined by multiplying both values. These values were re-ranked and genes were categorized as highly likely (for the top 103 mutational events—10 genes), very likely (103 mutational events/18 genes), likely (102 mutational events/31 genes), and possible (124 mutational events/43 genes) motility genes. Two genes were eliminated from further consideration where the number of synonymous mutations was far greater in the unselected than in the selected group, as this difference is not expected to contribute to motility.

Isolation of Spontaneous Suppressors of Non-Motile *E. acetylicum* Strains.

To identify spontaneous suppressors of non-motile mutant strains, each non-motile mutant strain was grown independently in BHI broth overnight, and 10 µL of the resulting culture was streaked on the center of 0.3% agar BHI plates and incubated overnight. Bacteria at the edge of the growth zone were collected and re-inoculated in the center of another 0.3% agar plate. The cycle was repeated until a clear enrichment for motile variants was observed. Rifampin (Rif) resistant variants of these non-motile mutants were isolated, and their suppressors, by plating saturated cultures on BHI plates supplemented with 1 µg/mL rifampin. The selection for RifR variants did not affect the mutants or their suppressor's motility status.

Gnotobiotic Zebrafish Colonization.

All zebrafish experiments were conducted in conformity with the Public Health Service Policy on Humane Care and Use of Laboratory Animals using protocols approved by the Institutional Animal Care and Use Committee of Duke University. Derivation and colonization of germ-free zebrafish (Tübingen strain) was performed as described with the following exceptions. Germ-free zebrafish were reared in sterile tissue culture flasks in 30 mL Gnotobiotic Zebrafish Medium (GZM) and received daily 83.3% media changes starting at 6 days post-fertilization (dpf). Starting at 5 dpf, larvae were fed approximately 2.5 mg/day with a custom-formulated diet consisting of, by mass, 45% protein, 15.07% fat, 12.09% carbohydrate, 0.97% fiber, 4× vitamin supplement, 19.57% ash (ZEIGLER BROTHERS INC.), pelleted and sterilized by irradiation (absorbed dose range 106.5-135.2 kGy; NEUTRON PRODUCTS INC.) At 6 dpf, overnight shaking cultures of *E. acetylicum* motile and non-motile rifampin-resistant and rifampin-sensitive strains were mixed in 1:500 ratios. Each strain mixture was pelleted and resuspended in 450 µl of sterile PBS for every 1 ml of strain mixture that was pelleted. Subsequently, zebrafish larvae were colonized by immersion as follows: 83.3% of the media was removed from each flask, leaving 5 ml GZM, and 400 µl of one of the bacterial mixture suspensions was added to each flask, resulting in an inoculum concentration of 1-6×10$^8$ CFU/ml. After 30 minutes of immersion in the *E. acetylicum* strain mixtures, 25 ml GZM was added to each flask. Each flask subsequently underwent three consecutive 83.3% media changes. To assess whole larvae bacterial loads, larvae at 3 days post-inoculation (d.p.i) were euthanized via tricaine overdose (sterile-filtered buffered tricaine at 0.83 mg/ml) and individual larvae were homogenized in 500 µL PBS using a Tissue-Tearor (BIOSPEC) for 1 min at maximum speed. Multiple dilutions of each larval homogenate from the respective flask were plated on BHI with or without 1 µg/ml rifampin. The number of colony forming units were assessed after overnight growth at 28° C.

Various features and advantages of the invention are set forth in the following claims.

All references, including publications, patent applications, and patents, cited herein are hereby incorporated by reference to the same extent as if each reference were individually and specifically indicated to be incorporated by reference and were set forth in its entirety herein.

Preferred embodiments of this invention are described herein, including the best mode known to the inventors for carrying out the invention. Variations of those preferred embodiments may become apparent to those of ordinary skill in the art upon reading the foregoing description. The inventors expect skilled artisans to employ such variations as appropriate, and the inventors intend for the invention to be practiced otherwise than as specifically described herein. Accordingly, this invention includes all modifications and equivalents of the subject matter recited in the claims appended hereto as permitted by applicable law. Moreover, any combination of the above-described elements in all possible variations thereof is encompassed by the invention unless otherwise indicated herein or otherwise clearly contradicted by context.

What is claimed is:

1. A method of identifying a genetic regulator of motility affecting host colonization, the method comprising:
   contacting *Exiguobacterium* with a mutagen in vitro to produce a plurality of mutagenic variants;
   performing a low-melt agar, swarming based assessment of the mutagenic *Exiguobacterium* variants and isolating those that are non-motile;

sequencing at least a portion of the plurality of non-motile mutagenic *Exiguobacterium* variants' genomes; and determining differences in the genomic sequences of the plurality of non-motile mutagenic *Exiguobacterium* variants as compared to a reference genome, wherein the differences in the genomic sequences between the plurality of mutagenic variants and the reference genome are used to identify a genetic regulator of motility affecting host colonization.

2. The method of claim 1, further comprising performing bioinformatics analysis to identify known genetic regulators of motility, and determining differences between the sequences of the known genetic regulators and the genomic sequences of the plurality of mutagenic variants.

3. The method of claim 1, further comprising performing suppression-bases analysis of the plurality of mutagenic variants comprising:

passaging one or more of the plurality of mutagenic variants at least three times; and performing phenotype-based assessment of the one or more of the plurality of mutagenic variants to identify variants exhibiting the desired phenotype based on motility.

4. The method of claim 1, wherein the mutagen is a selected from the group consisting of ethyl methyl sulfonate (EMS), methyl methane sulphonate (MMS), nitrous acid, N-ethyl-N'-nitro-N-nitrosoguanidine (ENNG), 1,2-dibromoethane (DBE), 1-chloro-2,4-dinitrobenzene (CDNB), styrene-7,8-oxide (STOX), N-ethyl-N-nitrosourea (ENU), radiation and ultraviolet light.

5. The method of claim 1, wherein sequencing at least a portion of the plurality of mutagenic variants' genomes comprises determining mutagen-induced single nucleotide variants (SNVs).

6. The method of claim 1, wherein performing a low-melt agar based assessment of the mutagenic variants comprises identifying the mutagenic variants that are non-motile.

7. The method of claim 1, wherein the genetic regulator is a gene known to be involved in flagellar function.

8. The method of claim 7, wherein the genetic regulator is selected from the group consisting of: fliE, fliF, fliK, flgG1, flhA, fliM, flgN, and hag1.

9. The method of claim 1, wherein the genetic regulator is a gene not known to be involved in motility.

10. The method of claim 9, wherein the genetic regulator is selected from the group consisting of: ftsX, ea2619, ea2862, and ea2157.

11. The method of claim 1, wherein the host is a human.

* * * * *

SEQUENCE LISTING

```
<160> NUMBER OF SEQ ID NOS: 7

<210> SEQ ID NO 1
<211> LENGTH: 5
<212> TYPE: PRT
<213> ORGANISM: Unknown
<220> FEATURE:
<223> OTHER INFORMATION: Diguanylate cyclase domain

<400> SEQUENCE: 1

Gly Gly Asp Glu Phe
1               5

<210> SEQ ID NO 2
<211> LENGTH: 3
<212> TYPE: PRT
<213> ORGANISM: Unknown
<220> FEATURE:
<223> OTHER INFORMATION: Phosphodiesterase domain

<400> SEQUENCE: 2

Glu Ala Leu
1
```

```
<210> SEQ ID NO 3
<211> LENGTH: 3
<212> TYPE: PRT
<213> ORGANISM: Unknown
<220> FEATURE:
<223> OTHER INFORMATION: Signal transduction sensor

<400> SEQUENCE: 3

Pro Ala Ser
1

<210> SEQ ID NO 4
<211> LENGTH: 4
<212> TYPE: PRT
<213> ORGANISM: Unknown
<220> FEATURE:
<223> OTHER INFORMATION: Bacterial signaling domain

<400> SEQUENCE: 4

Met Tyr His Thr
1

<210> SEQ ID NO 5
<211> LENGTH: 26
<212> TYPE: DNA
<213> ORGANISM: Artificial sequence
<220> FEATURE:
<223> OTHER INFORMATION: Ribosome site for cheY

<400> SEQUENCE: 5
tgttctaagg aggaactaat atgagt                                              26

<210> SEQ ID NO 6
<211> LENGTH: 27
<212> TYPE: DNA
<213> ORGANISM: Artificial sequence
<220> FEATURE:
<223> OTHER INFORMATION: Ribosome site for flhA

<400> SEQUENCE: 6
aaaatgaaag gatgaagcat catgagt                                             27

<210> SEQ ID NO 7
<211> LENGTH: 23
<212> TYPE: DNA
<213> ORGANISM: Artificial sequence
<220> FEATURE:
<223> OTHER INFORMATION: Intergenic region between rutD3 and ea3382

<400> SEQUENCE: 7
gacaatgaaa agagcgctca gcg                                                 23
```